US012582538B2

(12) United States Patent
Gifford, III et al.

(10) Patent No.: US 12,582,538 B2
(45) Date of Patent: Mar. 24, 2026

(54) EXPANDABLE DEVICES AND ASSOCIATED SYSTEMS AND METHODS

(71) Applicant: The Foundry, LLC, Menlo Park, CA (US)

(72) Inventors: Hanson S. Gifford, III, Woodside, CA (US); Edward DeWitt Gifford, Glastonbury, CT (US); Vrad W. Levering, Smithville, TX (US)

(73) Assignee: The Foundry, LLC, Menlo Park, CA (US)

( * ) Notice: Subject to any disclaimer, the term of this patent is extended or adjusted under 35 U.S.C. 154(b) by 672 days.

(21) Appl. No.: 17/907,034

(22) PCT Filed: Mar. 24, 2021

(86) PCT No.: PCT/US2021/070307
§ 371 (c)(1),
(2) Date: Sep. 22, 2022

(87) PCT Pub. No.: WO2021/195665
PCT Pub. Date: Sep. 30, 2021

(65) Prior Publication Data
US 2023/0118855 A1      Apr. 20, 2023

Related U.S. Application Data

(60) Provisional application No. 62/993,859, filed on Mar. 24, 2020.

(51) Int. Cl.
*A61F 2/91*       (2013.01)
*A61F 2/24*       (2006.01)
(Continued)

(52) U.S. Cl.
CPC ............ *A61F 2/915* (2013.01); *A61F 2/2418* (2013.01); *A61F 2/2433* (2013.01); *A61F 2/852* (2013.01);
(Continued)

(58) Field of Classification Search
CPC ...... A61F 2/915; A61F 2/2418; A61F 2/2433; A61F 2/852; A61F 2/958;
(Continued)

(56) References Cited

U.S. PATENT DOCUMENTS 5,496,365 A     3/1996  Sgro
5,591,197 A     1/1997  Orth et al.
(Continued)

FOREIGN PATENT DOCUMENTS

CA        2634358 A1     6/2007
CN        112618121 A    4/2021
(Continued)

OTHER PUBLICATIONS

International Search Report and Written Opinion dated Jul. 29, 2021; International Application No. PCT/US21/70307; 14 pages.

*Primary Examiner* — Suzette J Gherbi
(74) *Attorney, Agent, or Firm* — FORTEM IP LLP

(57)          ABSTRACT

Expandable devices are disclosed herein. Several of the embodiments are directed towards an expandable device comprising a stent configured to be expanded within a body conduit of a human patient. The stent may comprise a tubular sidewall having first portions and second portions. Radial expansion of the stent may cause the first portions to bow outwardly and out of radial alignment with the second portions.

18 Claims, 31 Drawing Sheets

(51) Int. Cl.
  *A61F 2/852*        (2013.01)
  *A61F 2/915*        (2013.01)
  *A61F 2/958*        (2013.01)
  *A61F 2/00*         (2006.01)

(52) U.S. Cl.
  CPC ...... *A61F 2/958* (2013.01); *A61F 2002/0081*
      (2013.01); *A61F 2230/0069* (2013.01); *A61F*
      *2250/001* (2013.01)

(58) Field of Classification Search
  CPC ...... A61F 2002/0081; A61F 2230/0069; A61F
      2250/001; A61F 2/848; A61F 2002/825;
      A61F 2002/91575; A61F 2250/0039;
      A61F 2250/0048
  See application file for complete search history.

(56) References Cited

U.S. PATENT DOCUMENTS

| | | | |
|---|---|---|---|
| 5,681,346 A | 10/1997 | Orth et al. | |
| 5,733,325 A | 3/1998 | Robinson et al. | |
| 5,735,871 A | 4/1998 | Sgro | |
| 5,853,419 A | 12/1998 | Imran | |
| 6,206,910 B1 | 3/2001 | Berry et al. | |
| 6,206,916 B1 | 3/2001 | Furst | |
| 7,118,600 B2 | 10/2006 | Dua et al. | |
| 7,815,673 B2 | 10/2010 | Bloom et al. | |
| 8,114,152 B2 | 2/2012 | Furst | |
| 8,696,729 B2 | 4/2014 | Thompson et al. | |
| 8,894,702 B2 | 11/2014 | Quadri et al. | |
| 10,238,339 B2 | 3/2019 | Dlugach et al. | |
| 10,470,881 B2 | 11/2019 | Noe et al. | |
| 10,925,706 B2 | 2/2021 | Eigler et al. | |
| 11,291,807 B2 | 4/2022 | Eigler et al. | |
| 11,812,930 B2 | 11/2023 | Jen et al. | |
| 11,850,138 B2 | 12/2023 | Eigler et al. | |
| 2001/0011188 A1 | 8/2001 | Berry et al. | |
| 2002/0052646 A1 | 5/2002 | Fischell et al. | |
| 2002/0055767 A1 | 5/2002 | Forde et al. | |
| 2003/0105517 A1* | 6/2003 | White | A61F 2/91 |
| | | | 623/1.16 |
| 2005/0038501 A1 | 2/2005 | Moore et al. | |
| 2005/0080478 A1 | 4/2005 | Barongan | |
| 2007/0213813 A1 | 9/2007 | Von et al. | |
| 2007/0239261 A1 | 10/2007 | Bose et al. | |
| 2008/0077228 A1 | 3/2008 | Goto | |
| 2008/0234800 A1 | 9/2008 | Clarke | |
| 2009/0248132 A1* | 10/2009 | Bloom | A61F 2/852 |
| | | | 623/1.15 |
| 2009/0248133 A1 | 10/2009 | Bloom et al. | |
| 2009/0270972 A1 | 10/2009 | Lane | |
| 2010/0174309 A1 | 7/2010 | Fulkerson et al. | |

| | | | |
|---|---|---|---|
| 2011/0106234 A1 | 5/2011 | Grandt | |
| 2011/0238154 A1 | 9/2011 | Murphy et al. | |
| 2011/0251674 A1 | 10/2011 | Schmid et al. | |
| 2012/0116498 A1* | 5/2012 | Chuter | A61F 2/2412 |
| | | | 623/1.26 |
| 2014/0180384 A1 | 6/2014 | Leblanc et al. | |
| 2014/0200655 A1 | 7/2014 | Webler et al. | |
| 2014/0277345 A1 | 9/2014 | Havel et al. | |
| 2014/0277562 A1 | 9/2014 | Seddon et al. | |
| 2015/0216552 A1 | 8/2015 | Hefer | |
| 2015/0265438 A1 | 9/2015 | Hossainy et al. | |
| 2016/0296327 A1 | 10/2016 | Eberhardt et al. | |
| 2017/0172771 A1 | 6/2017 | Bruckheimer et al. | |
| 2017/0231765 A1 | 8/2017 | Desrosiers et al. | |
| 2017/0325948 A1 | 11/2017 | Wallace et al. | |
| 2017/0340434 A1 | 11/2017 | Cerchiari et al. | |
| 2017/0340460 A1 | 11/2017 | Rosen et al. | |
| 2018/0206986 A1 | 7/2018 | Noe et al. | |
| 2018/0344994 A1 | 12/2018 | Karavany et al. | |
| 2019/0110911 A1 | 4/2019 | Nae et al. | |
| 2019/0175105 A1 | 6/2019 | Dlugach et al. | |
| 2019/0262118 A1 | 8/2019 | Eigler et al. | |
| 2019/0262129 A1 | 8/2019 | Cooper et al. | |
| 2020/0229956 A1 | 7/2020 | Jackson et al. | |
| 2020/0375721 A1 | 12/2020 | Celermajer et al. | |
| 2021/0154032 A1 | 5/2021 | Welch | |
| 2021/0161637 A1 | 6/2021 | Eigler et al. | |
| 2021/0308433 A1 | 10/2021 | Gifford, III et al. | |
| 2021/0353300 A1 | 11/2021 | Kottenmeier et al. | |
| 2022/0175561 A1 | 6/2022 | Doyle et al. | |
| 2022/0211492 A1 | 7/2022 | Pintor et al. | |
| 2022/0346988 A1 | 11/2022 | Okereke et al. | |
| 2023/0105665 A1* | 4/2023 | Gifford, III | A61F 2/915 |
| | | | 72/58 |
| 2023/0110800 A1 | 4/2023 | Dienno, V | |
| 2023/0115137 A1* | 4/2023 | Gifford, III | A61F 2/06 |
| | | | 623/1.15 |
| 2023/0172757 A1 | 6/2023 | Willner et al. | |
| 2023/0285172 A1 | 9/2023 | King et al. | |
| 2024/0216135 A1 | 7/2024 | Montorfano | |
| 2024/0261101 A1 | 8/2024 | Mulligan et al. | |
| 2024/0398420 A1 | 12/2024 | Dahan et al. | |

FOREIGN PATENT DOCUMENTS

| | | | |
|---|---|---|---|
| EP | 3248645 A1 | 11/2017 | |
| WO | 2018131043 A1 | 7/2018 | |
| WO | 2020033933 A1 | 2/2020 | |
| WO | 2020254835 A1 | 12/2020 | |
| WO | 2021195305 A1 | 9/2021 | |
| WO | 2021195664 A1 | 9/2021 | |
| WO | 2023091938 A1 | 5/2023 | |
| WO | 2023137000 A1 | 7/2023 | |

* cited by examiner

AORTA

AORTIC
VALVE

1300

200

101

AORTA

B

B

101

14B

B

B

200

LEAFLET

14B

100

150

150

108

LEAFLET

106b

106a

106a

106b t

200

LEAFLET

LEAFLET

LEAFLET

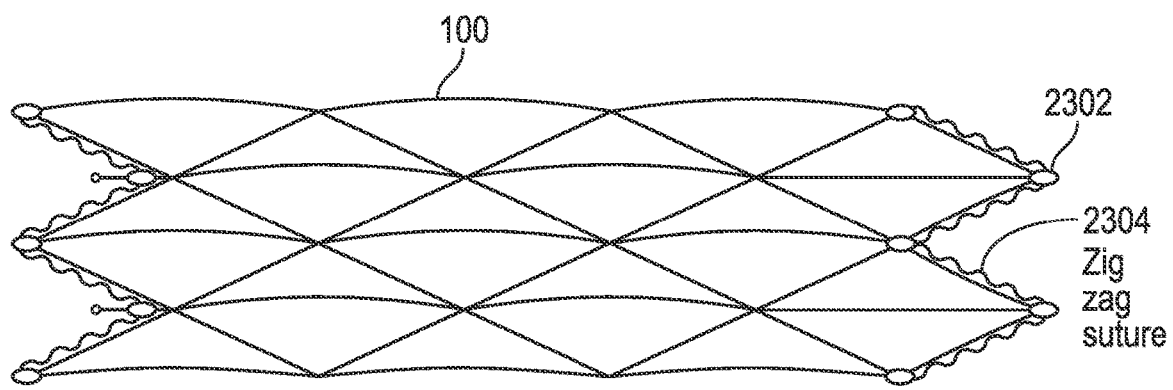
_FIG. 23A_
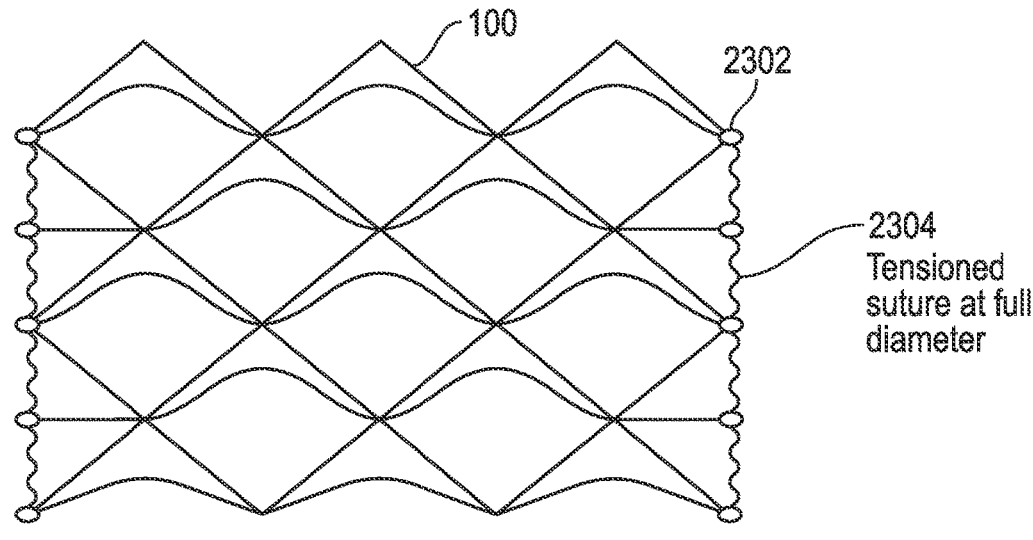
_FIG. 23B_

Tubing to hold ends down

Sock collapses shut in diastole

200

101

2502
Wind sock tubing

System blood flow

200

101

2602
Cone shaped wind sock

2802
Loops formed
on ends of
stent struts

EXPANDABLE DEVICES AND ASSOCIATED SYSTEMS AND METHODS

CROSS-REFERENCE TO RELATED APPLICATION(S)

The present application is a 371 U.S. national phase application of International Application No. PCT/US2021/070307, filed Mar. 24, 2021, which claims the benefit of priority to U.S. Patent Application No. 62/993,845, filed Mar. 24, 2020, which are incorporated herein by reference in their entireties.

TECHNICAL FIELD

The present technology relates to expandable devices and associated systems and methods. In particular embodiments, the present technology relates to devices for treating body conduits, such as blood vessels and heart valves, and associated systems and methods of use.

BACKGROUND

There are many situations in interventional vascular procedures where there is a need to inflate a balloon in a vessel while maintaining perfusion through that vessel. For example, when delivering a balloon-expandable stent in a coronary artery, it is preferable to maintain blood flow through the artery to avoid ischemic damage to the myocardium perfused by that artery. One device commonly used to maintain blood flow is a perfusion balloon catheter. These catheters typically have a relatively large central guidewire lumen with holes through the catheter sidewall into the lumen just proximal to the balloon. This allows blood to flow through the side holes, into the guidewire lumen, and out the distal end of the catheter to maintain perfusion when the balloon is inflated and occluding the vessel.

However, these perfusion balloons are typically only used in smaller vessels where a relatively small perfusion lumen is sufficient and the catheter can be made with a perfusion lumen of a fixed size, for example a lumen of less than 2 mm in diameter. In larger vessels such as the aorta, maintaining adequate distal perfusion without a high pressure gradient through the perfusion lumen requires a much larger lumen.

Two common interventional procedures that utilize balloon expansion are (a) balloon valvuloplasty of the aortic valve, and (b) catheter-based delivery of balloon-expandable replacement aortic valves (commonly referred to as "transcatheter aortic valve replacement" or "TAVR"). Conventional practice is to inflate the balloon to a large diameter (about 20-30 mm) at a very high pressure, blocking all flow to the systemic circulation. It also prevents any blood from leaving the left ventricle, which can lead to a dangerous acute expansion of the ventricle. In order to prevent this dangerous expansion of the left ventricle, a temporary pacing catheter is placed in the heart and the heart is typically paced at a very high rate (~200 beats per minute) which prevents the left ventricle from filling between heartbeats. Such rapid ventricular pacing may cause myocardial ischemia, malignant arrhythmias, low output, reduced cerebral oxygen saturation, and/or increased procedure time and risk of stroke. To avoid or reduce the likelihood of these dangers, the valvuloplasty or TAVR balloon is typically inflated for less than a minute.

In a typical balloon catheter, the balloon is formed from a single extrusion which is expanded into the desired balloon shape and welded or bonded to the shaft of a catheter. The sidewall of the catheter is cut to create an opening to connect an inflation lumen running through the catheter shaft to the interior of the balloon. In most clinical applications in which a vessel or valve is being dilated, the outer surface of the balloon is rounded (i.e., has a functionally circular cross-sectional shape) so as to apply a relatively even radial force against the apposing tissue. It is difficult to locate a perfusion lumen at the outer circumference of the balloon while maintaining this rounded/circular shape and providing an even radially outward force.

An existing approach to the foregoing challenge of creating a large perfusion lumen in larger balloon catheters is the TRUE® Flow Valvuloplasty Perfusion Catheter (C.R. Bard/Becton Dickenson). The TRUE® Flow device has several smaller balloons arranged around the periphery of a central lumen and surrounded by a fiber-based shell. When inflated, the balloons hold the central lumen open. However, this approach limits the effective pressure which can be applied to the circumference of the balloon, even when these smaller balloons are inflated to a higher pressure. More importantly, the use of multiple balloons employs a large amount of material which increases the deflated diameter of the device and makes delivery of the device through a delivery sheath more difficult. This is especially true in the case of a TAVR balloon that has the additional bulk of the prosthetic valve.

Therefore, there remains a need for improved expandable devices for interventional procedures, especially within the field of interventional cardiology.

SUMMARY

The expandable devices of the present technology comprise tubular sidewalls having portions configured to bow out of alignment with the rest of the sidewall as the device is expanded. The expandable devices and/or stents of the present technology may have many applications, among which are vascular stents and stent-grafts, valvuloplasty and vascular dilatation systems, and stent-valve delivery systems. The undulating topography of the expandable devices of the present technology may provide many clinical benefits over conventional devices, as discussed herein. Among these benefits is the creation of an annular perfusion lumen that allows blood flow past the balloon catheter system while the balloon is expanded in a blood flow passage or other body conduit.

The subject technology is illustrated, for example, according to various aspects described below, including with reference to FIGS. 2A-29. Various examples of aspects of the subject technology are described as numbered clauses (1, 2, 3, etc.) for convenience. These are provided as examples and do not limit the subject technology.

1. An expandable device comprising:
   a stent comprising a tubular sidewall, the sidewall of the stent having first portions and second portions, wherein the stent has a collapsed configuration and an expanded configuration in which the device is configured to be positioned within a body conduit of a human patient at a treatment site,
   wherein transformation of the stent from the collapsed configuration to the expanded configuration causes the first portions of the sidewall to bow out of a cylindrical surface defined by the second portions of the sidewall such that, at least in the expanded configuration, the first portions form a plurality of buckled regions extending radially away from the second portions of the sidewall.

2. The expandable device of Clause 1, wherein the buckled regions are spaced apart about a circumference of the stent.

3. The expandable device of Clause 1 or Clause 2, wherein the buckled regions are spaced apart along a length of the stent.

4. The expandable device of any one of Clauses 1 to 3, wherein the buckled regions are disposed only at one or both of the first and second end portions of the stent.

5. The expandable device of any one of Clauses 1 to 3, wherein the buckled regions are disposed only along an intermediate portion of the stent.

6. The expandable device of any one of Clauses 1 to 5, wherein, when the stent is in a collapsed configuration, the first and second portions are generally radially aligned such that the sidewall has a substantially cylindrical shape.

7. The expandable device of any one of Clauses 1 to 6, wherein, when the stent is in an expanded configuration, the second portions are generally radially aligned along a length of the stent and the first portions are radially offset from the second portions.

8. The expandable device of any one of Clauses 1 to 7, wherein, when the stent is in an expanded configuration, at least some of the buckled regions extend radially outwardly from the second portions.

9. The expandable device of any one of Clauses 1 to 8, wherein, when the stent is in an expanded configuration, at least some of the buckled regions extend radially inwardly from the second portions.

10. The expandable device of any one of Clauses 1 to 9, wherein, when the stent is in an expanded configuration, the buckled regions comprise arched protrusions, and wherein each of the arched protrusions have (a) first and second end portions coupled to one of the second portions and (b) a peak region between the first and second end portions, the peak region comprising a portion of the buckled region that is radially farthest from the first and second end portions.

11. An expandable device comprising:

a stent having a collapsed configuration and an expanded configuration in which the stent is configured to be positioned in a body conduit of a patient, the stent comprising a plurality of spines and a plurality of struts, the spines extending along a longitudinal axis of the stent and the struts extending between circumferentially adjacent spines, each of the spines having first portions and second portions along a respective length of the spine, wherein:

in the collapsed configuration, the struts and the spines are substantially the same radial distance from a central longitudinal axis of the stent and together define a substantially cylindrical surface surrounding a lumen, and in the expanded configuration, (a) the struts and the first portions of the spines are a first radial distance from the central longitudinal axis, and (b) the second portions of the spines are a second radial distance from the central longitudinal axis, the second radial distance different than the first radial distance.

12. The expandable device of Clause 11, wherein, when in the expanded configuration, the stent includes an annular lumen between (a) the second portions of the spines and (b) the struts and the first portions of the spines.

13. The expandable device of Clause 12, wherein, when the stent is in the expanded configuration, the struts and the first portions of the spines together define an expanded lumen through the stent, and wherein the annular lumen surrounds the expanded lumen.

14. The expandable device of Clause 12, wherein, when the stent is in the expanded configuration, the second portions of the stent together define an expanded lumen through the stent, and wherein the annular lumen surrounds the expanded lumen.

15. The expandable device of any one of Clauses 11 to 13, wherein the second radial distance is greater than the first radial distance.

16. The expandable device of any one of Clauses 11, 12, or 14, wherein the second radial distance is less than the first radial distance.

17. The expandable device of any one of Clauses 11 to 14, wherein the second radial distance for some of the second portions is less than the first radial distance, and the second radial distance for others of the second portions is greater than the first radial distance.

18. The expandable device of any one of Clauses 11 to 17, wherein the spines are substantially linear in the collapsed configuration and have an undulating shape in the expanded configuration.

19. An expandable device comprising:

a stent having a collapsed configuration and an expanded configuration in which the stent is configured to be positioned in a body conduit of a patient, the stent comprising a plurality of spines and a plurality of struts, the spines extending along a longitudinal axis of the stent and the struts connecting adjacent spines, wherein:

the spines include a spine having first and second end portions, the struts include a first strut and a second strut— the first strut having first and second end portions, wherein the first end portion of the first strut is connected to the first end portion of the spine, the second strut having first and second end portions, wherein the second end portion of the second strut is connected to the second end portion of the spine, and wherein radial expansion of the stent decreases a longitudinal distance between the first end portion of the first strut and the second end portion of the second strut, and decreases a longitudinal distance between the first and second end portions of the spine, thereby causing the spine to buckle out of radial alignment with the first and second struts.

20. The expandable device of Clause 19, wherein the first and second struts are substantially linear in the collapsed configuration and in the expanded configuration.

21. The expandable device of Clause 20, wherein each of the first and second struts connect to the spine at flexible joints.

22. The expandable device of any one of Clauses 19 to 21, wherein the spine is longer than a combined length of the first and second struts.

23. The expandable device of any one of Clauses 19 to 22, wherein, when the stent is in the collapsed configuration, the first and second struts are substantially parallel to the spine.

24. The expandable device of any one of Clauses 19 to 23, wherein a second end terminus of the first strut and a first end terminus of the second strut are fixed relative to one another at a node.

25. The expandable device of Clause 24, wherein another one of the spines is coupled to the node.

26. The expandable device of Clause 24 or Clause 25, wherein the spine is a first spine and the expandable device further comprises a second spine having first and second end portions, a third strut having first and second end portions, and a fourth strut having first and second end portions, and wherein— the first end portion of the third strut is coupled to the first end portion of the second spine and the second end portion of the third strut is coupled to the node, the first end portion of the fourth strut is coupled to the node and the second end portion of the fourth strut is coupled to the second end portion of the second spine, and radial expansion of the stent decreases a longitudinal distance between the first end portion of the third strut and the second end portion of the fourth strut, and decreases a longitudinal distance between the first and second end portions of the second spine, thereby causing the second spine to buckle out of radial alignment with the third and fourth struts.

27. The expandable device of Clause 26, wherein, when the stent is in the collapsed configuration, the first, second, third, and fourth struts are substantially parallel to the first and second spines.

28. The expandable device of Clause 26 or Clause 27, wherein, when the stent is in the expanded configuration, the first, second, third and fourth struts angle away from the first and second spines, thereby forming an X where the node is at the intersection of the X.

29. The expandable device of any one of Clauses 26 to 28, wherein, when the stent is in an expanded configuration, the node, the first strut, the second strut, the third strut, and the fourth strut are substantially radially aligned at a first radial location and the first and second spines are radially offset from the first radial location and disposed at a second radial location.

30. The expandable device of any one of Clauses 26 to 29, wherein a second end terminus of the third strut and a first end terminus of the fourth strut are fixed relative to one another at the node.

31. The expandable device of any one of Clauses 24 to 30, further comprising a third spine running longitudinally through and coupled to the node.

32. The expandable device of any one of the previous Clauses, wherein the expandable device is configured to be expanded via inflation of a balloon positioned within a central lumen of the stent.

33. The expandable device of any one of the previous Clauses, wherein the expandable device is configured to be expanded within a native heart valve.

34. The expandable device of any one of the previous Clauses, wherein the expandable device is configured to be expanded within the aorta.

35. The expandable device of any one of the previous Clauses, wherein the expandable device is configured to be expanded within the abdominal aorta.

36. The expandable device of any one of the previous Clauses, wherein the expandable device is configured to be expanded within a body lumen.

37. The expandable device of any one of the previous Clauses, wherein the expandable device is configured to be expanded within another stent.

38. The expandable device of any one of the previous Clauses, wherein the stent is coupled to a replacement valve.

39. The expandable device of any one of the previous Clauses, wherein the stent comprises a superelastic material.

40. The expandable device of any one of the previous Clauses, wherein the stent has been heat set at an intermediate expanded configuration, the intermediate expanded configuration having a diameter between a diameter of the stent in the collapsed configuration and a diameter of the stent in a fully expanded configuration.

41. The expandable device of any one of the previous Clauses, wherein the stent has been heat set at a fully expanded configuration.

42. The expandable device of any one of the previous Clauses, wherein the stent comprises a material that has been heat set.

43. A method for expanding a stent, the stent comprising a sidewall formed of a plurality of interconnected structural members including first connectors and second connectors, the second connectors extending between the first connectors, the method comprising:

increasing an arc length between circumferentially adjacent first connectors, thereby decreasing a longitudinal distance between first ends of longitudinally adjacent second connectors and increasing a circumferential distance between second ends of the longitudinally adjacent second connectors, wherein the first ends of the longitudinally adjacent second connectors are coupled to a same one of the first connectors, and wherein the same one of the first connectors comprises a buckling region between the first ends of the longitudinally adjacent second connectors;

longitudinally compressing the first connectors by decreasing the longitudinal distance between the first ends of the longitudinally adjacent second connectors; and forcing the buckling regions of the first connectors to bow out of radial alignment with the second connectors and other regions of the first connectors, thereby forming arched protrusions along the sidewall of the stent.

44. The method of Clause 42, further comprising positioning the stent in a blood flow passage of a patient in a collapsed configuration, and wherein— when the stent is in the collapsed configuration, the first and second connectors together define a main lumen of the stent, and wherein the method further comprises (a) expanding a balloon within the main lumen to expand the stent within the blood flow passage, thereby substantially blocking blood flow through the main lumen of the stent, and (b) creating an annular lumen around the main lumen, thereby allowing blood flow through the annular lumen while the balloon is blocking blood flow through the main lumen.

45. The method of Clause 42 or Clause 43, further comprising positioning the stent in a body conduit of a patient.

46. The method of any one of the previous Clauses, wherein, when the stent is in a collapsed configuration, the first and second connectors together define a main lumen of the stent, wherein the method further comprises expanding a balloon within the main lumen to increase the circumferential arc length between adjacent first connectors.

47. The method of any one of the previous Clauses, further comprising creating an annular lumen between (a) portions of the arched protrusions that are radially farthest from the central longitudinal axis of the stent and (b) the second connectors and other regions of the first connectors.

48. The method of any one of the previous Clauses, further comprising creating an annular lumen between (a) the circumference defined by the portions of the arched protrusions that are radially farthest from the central longitudinal axis of the stent and (b) the circumference defined by the second connectors and other regions of the first connectors.

49. The method of any one of the previous Clauses, wherein, when the stent is in a collapsed configuration, the first and second connectors are substantially the same radial distance from a central longitudinal axis of the stent and together define a main lumen of the stent.

50. The method of any one of the previous Clauses, wherein, when the stent is in the expanded configuration, (a) the second connectors and the other regions of the first connectors are a first radial distance from the central longitudinal axis, and (b) the buckling regions of the first connectors are a second radial distance from the central longitudinal axis different than the first radial distance.

51. The method of any one of the previous Clauses, wherein the stent is configured to be expanded within another stent.

52. The method of any one of the previous Clauses, wherein the stent is configured to be expanded within a native heart valve.

53. The method of any one of the previous Clauses, wherein the stent is configured to be expanded within the aorta.

54. The method of any one of the previous Clauses, wherein the stent is configured to be expanded within the abdominal aorta.

55. The method of any one of the previous Clauses, wherein the stent is configured to be expanded within a blood flow passage.

56. The expandable device of any one of Clauses 1 to 10, wherein, when the stent is in a collapsed configuration, the first and second portions are generally radially aligned such that the sidewall has substantially the same thickness as the tubing material from which the stent is constructed.

57. The expandable device of Clause 11, wherein, when in the expanded configuration, the stent defines an annular lumen between (a) the circumference described by the second portions of the spines and (b) the circumference described by the struts and the first portions of the spines.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

9 shown positioned at a native valve annulus in a collapsed configuration on a delivery device.

Figures 14A, 14B:
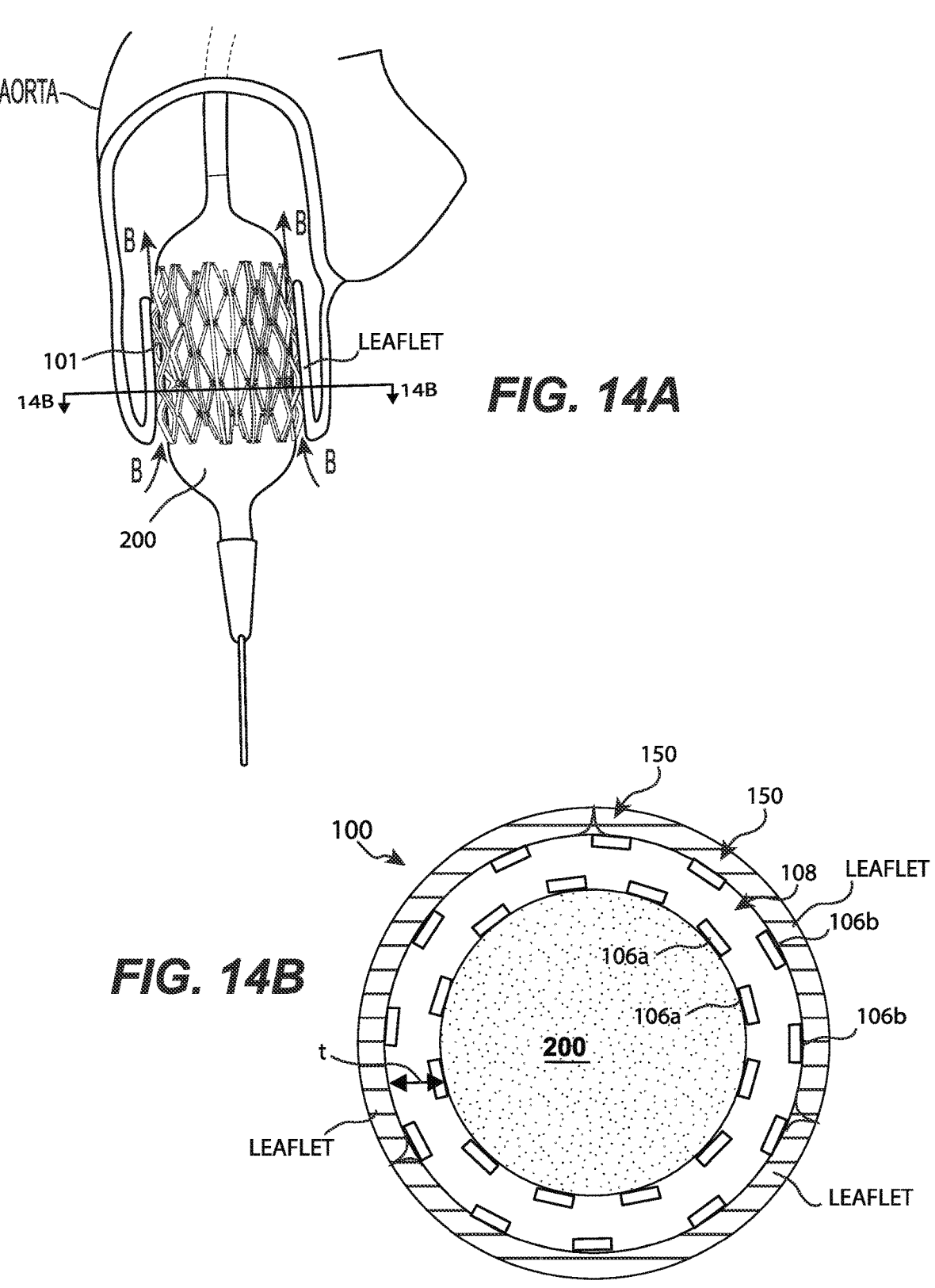

FIG. 14A illustrates an expandable device configured in accordance with embodiments of the present technology, shown positioned at a native valve annulus in an expanded configuration on a delivery device.

FIG. 14B is an axial cross-sectional view of the expandable device as shown positioned at a native valve annulus in FIG. 14A.

Figures 15, 16:
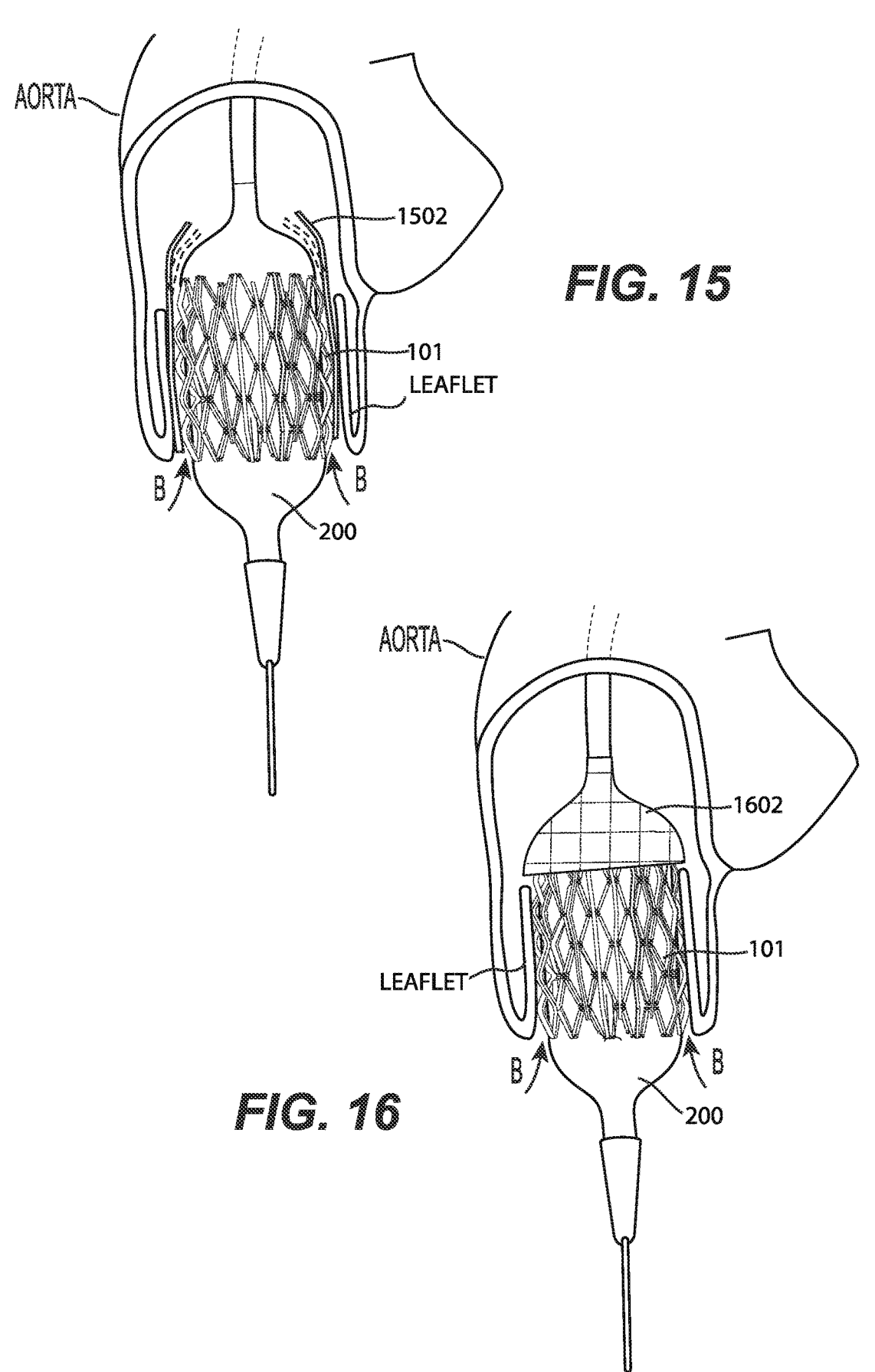

FIGS. 15 and 16 depict expandable devices configured in accordance with embodiments of the present technology, positioned at a native valve annulus.

Figures 17A, 17B:
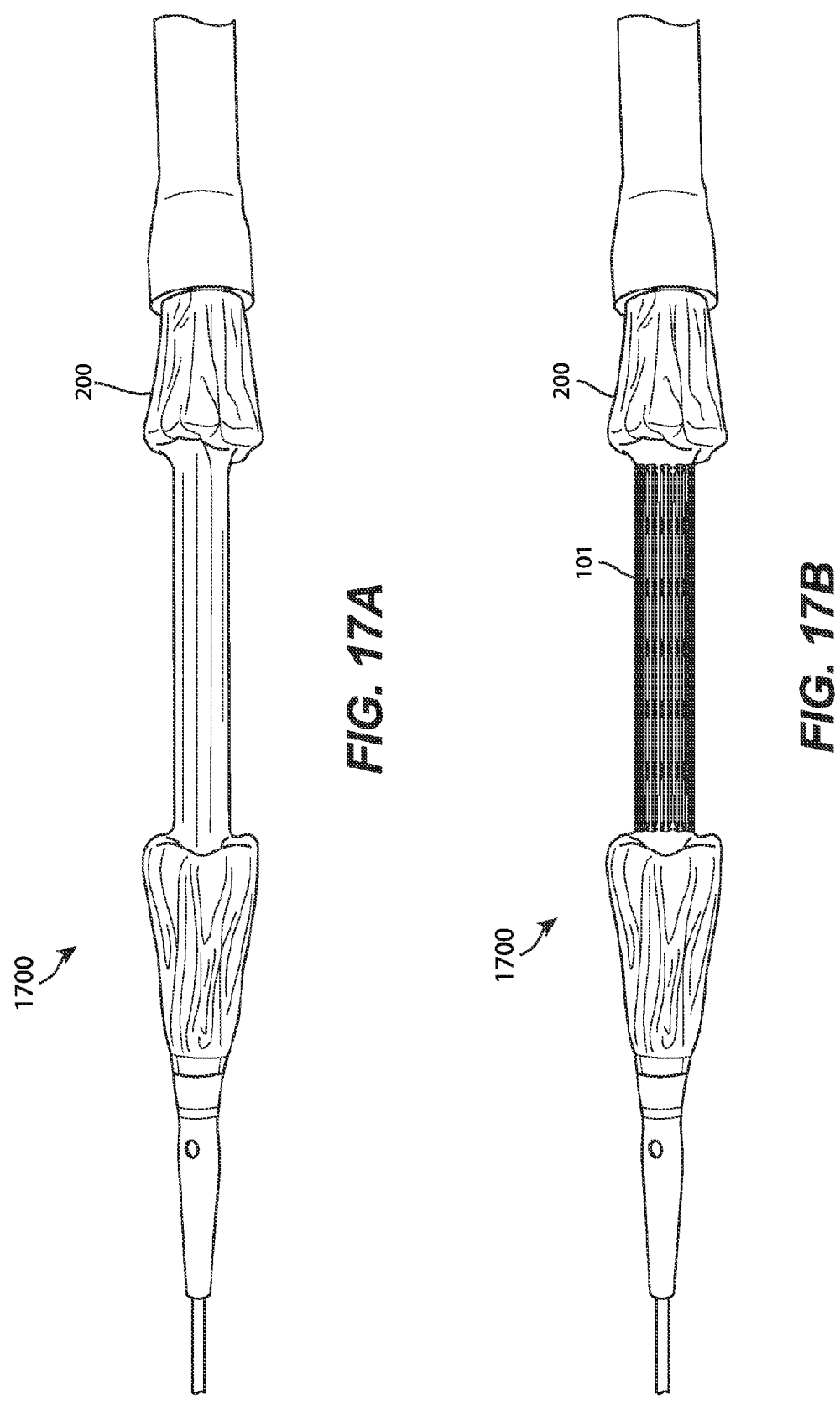

FIG. 17A is a side view of a distal portion of a delivery device configured in accordance with embodiments of the present technology.

FIG. 17B is a side view of an expandable device of the present technology in a collapsed configuration, shown positioned on the delivery device of FIG. 17A.

Figure 17C:
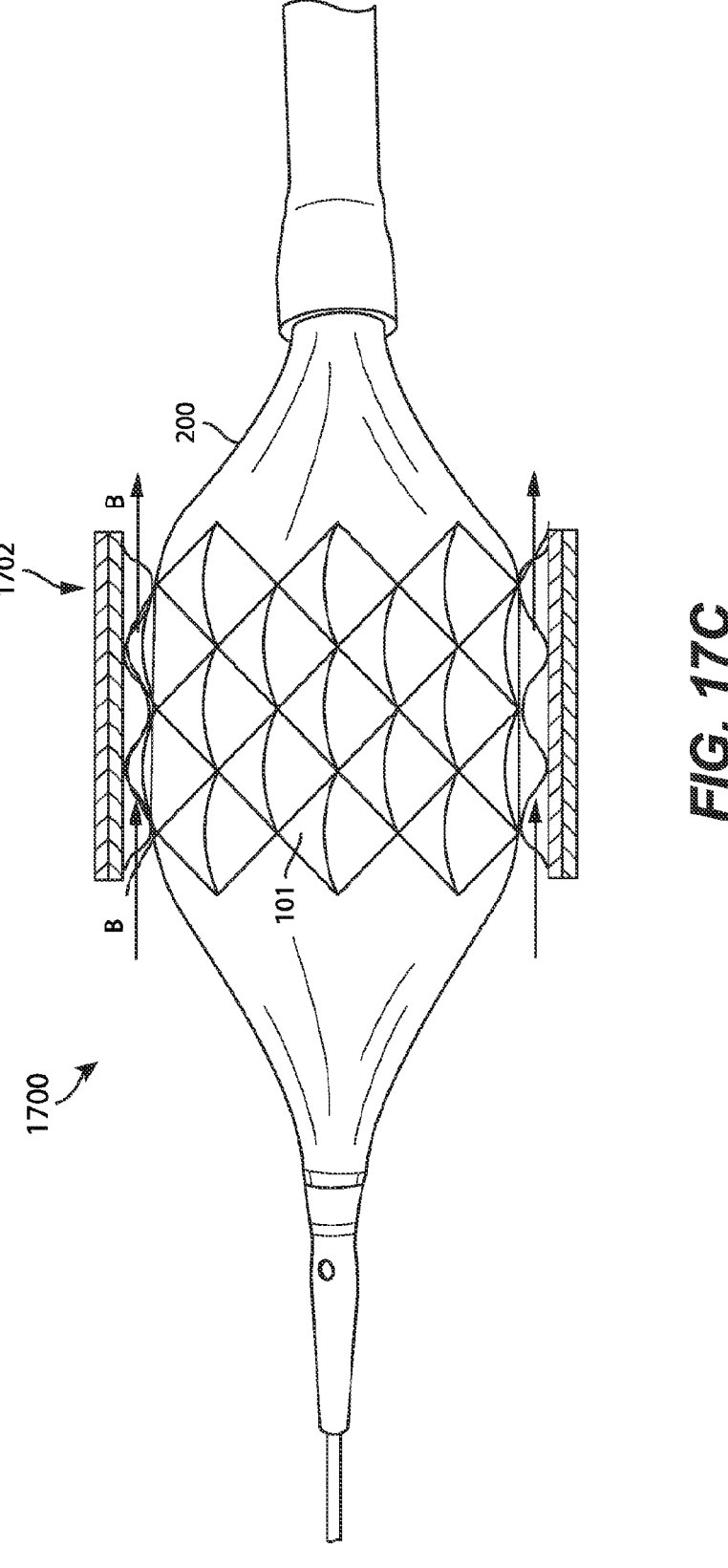

FIG. 17C is a side view of the delivery device and expandable device shown in FIG. 17B, with the expandable device in an expanded configuration.

Figures 18A, 18B:
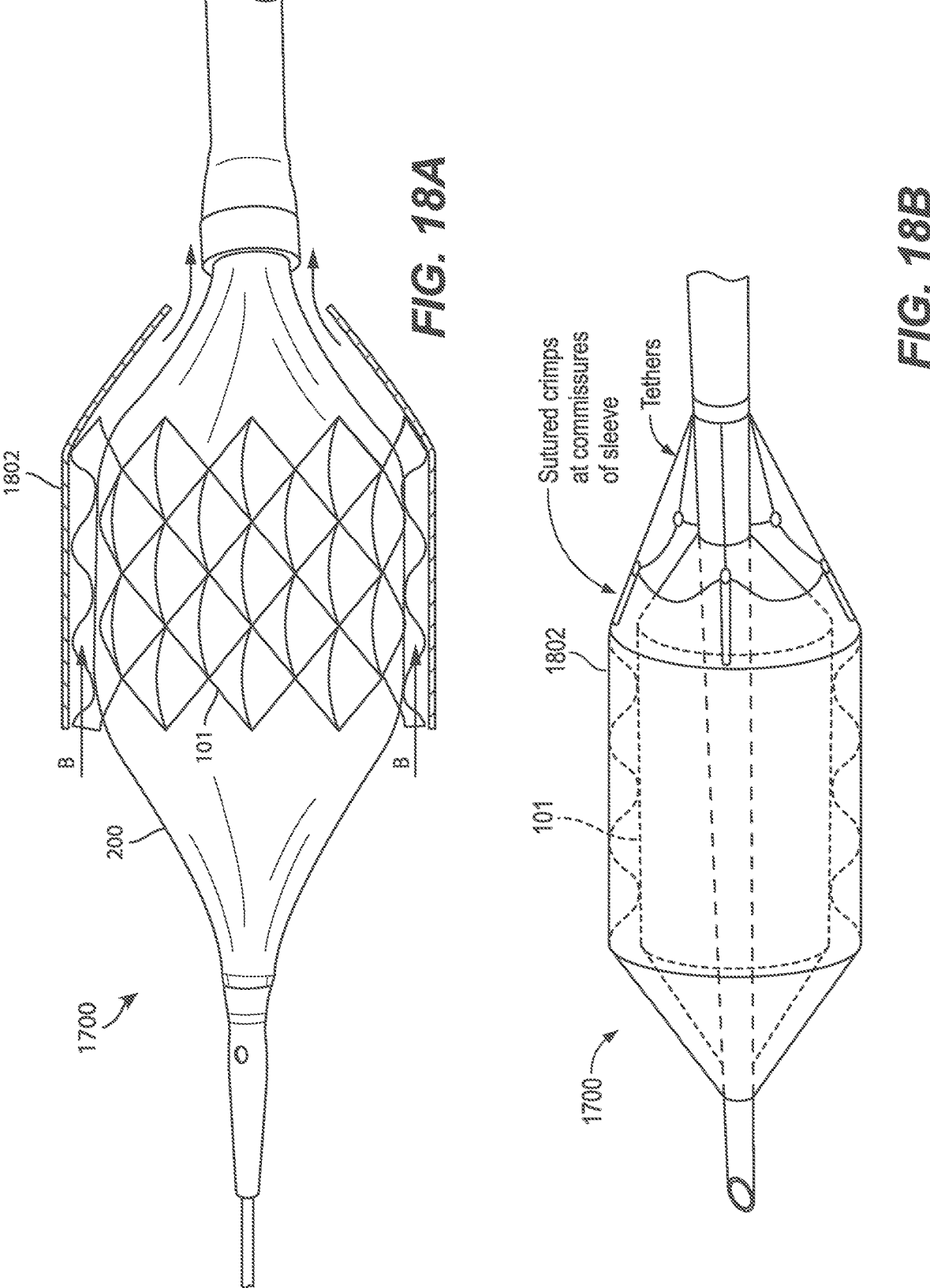

FIGS. 18A and 18B are side views of an expandable device configured in accordance with embodiments of the present technology, shown in an expanded configuration and positioned on a delivery device.

Figure 19A:
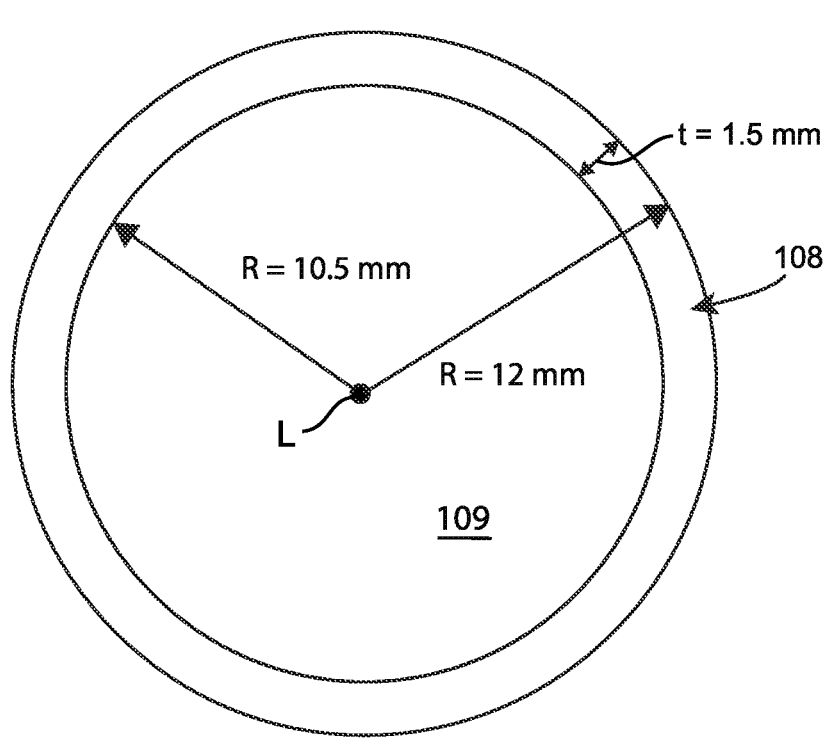
Figure 19B:
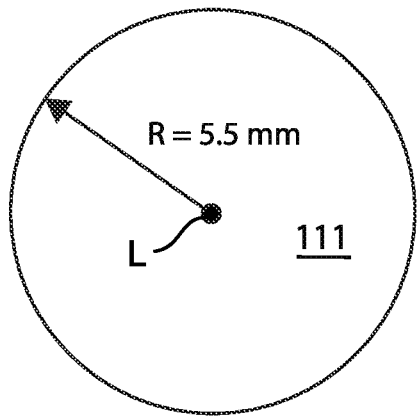

FIGS. 19A and 19B conceptually depict the cross-sectional area of an annular lumen created by the expandable devices of the present technology, as compared to a non-annular lumen.

FIGS. 20 and 21A-21C are side views of expandable devices configured in accordance with embodiments of the present technology.

Figure 22:
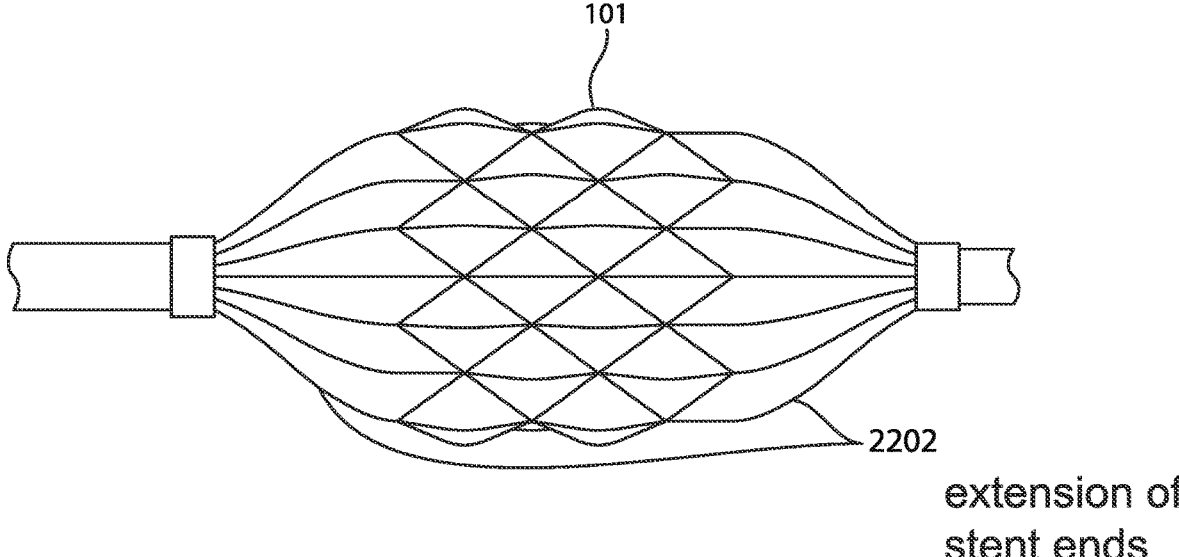

FIG. 22 shows an expandable device configured in accordance with several embodiments of the present technology.

FIGS. 23A and 23B show an expandable device configured in accordance with several embodiments of the present technology in a collapsed configuration and an expanded configuration, respectively.

FIGS. 24-28 depict several expandable devices configured in accordance with embodiments of the present technology.

Figure 29:
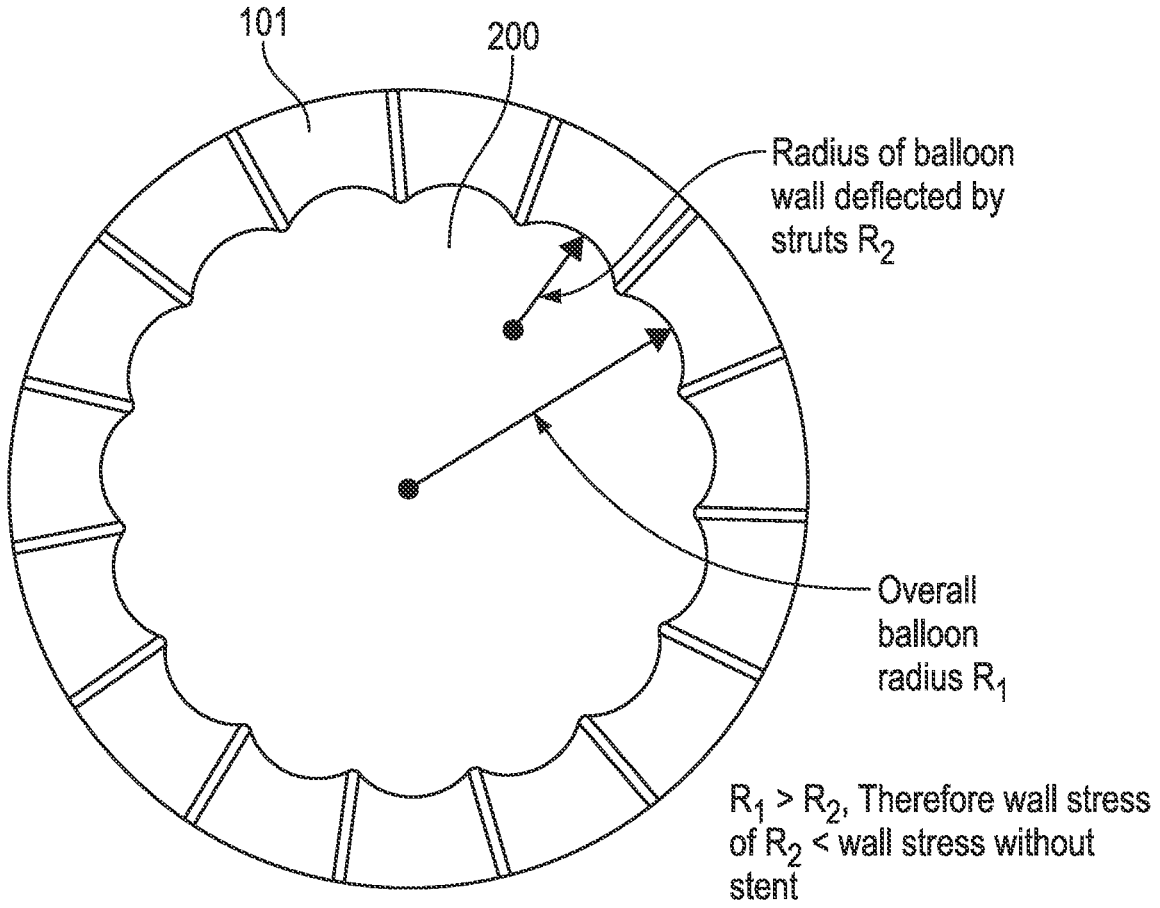

FIG. 29 is a conceptual illustration showing the interaction between a balloon and an expandable device of the present technology when the balloon and expandable device are in their respective expanded configurations.

DETAILED DESCRIPTION

The present technology relates to expandable treatment devices and associated systems and methods. Some embodiments of the present technology, for example, are directed to stents configured to be positioned within a body conduit. Specific details of several embodiments of the technology are described below with reference to FIGS. 2A-29.

I. Definitions

With regard to the terms "distal" and "proximal" within this description, unless otherwise specified, the terms can reference a relative position of the portions of an interventional device such as a prosthetic valve device and/or an associated delivery device with reference to an operator and/or a location in the vasculature or heart. For example, in referring to a delivery system including the perfusion devices described herein, "proximal" can refer to a position closer to the operator of the device or an incision into the vasculature, and "distal" can refer to a position that is more distant from the operator of the device or further from the incision along the vasculature (e.g., the end of the catheter).

As used herein, "stent" refers to an expandable medical device configured to be inserted into an anatomical vessel or passageway to provide support to the passageway and/or another medical device, and/or to modify biological tissue at the treatment site.

As used herein, the "collapsed configuration" refers to an unexpanded configuration of the expandable device and/or stent in which the expandable device and/or stent is configured to be delivered or withdrawn through a catheter to or from a treatment site. As used herein, the "expanded configuration" refers to a configuration of the expandable device and/or stent in which the expandable element is partially or fully expanded. An expanded configuration may be achieved via actuation only (for example, via inflation of a balloon), via self-expansion only, or both. In some embodiments, the stent may comprise a superelastic material and/or may be heat set to a desired shape, but the superelastic and/or heat set properties play a negligible role in expanding the stent. Unless provided otherwise herein, "fully expanded," as used to describe a configuration of the expandable device and/or stent, and/or a cross-sectional dimension of the expandable device and/or stent, refers to a configuration of the expandable device and/or stent at a diameter desired for treatment or facilitating treatment. For example, the fully expanded configuration and/or fully expanded diameter of the expandable device and/or stent may correlate with the fully expanded diameter of the balloon used to expand the expandable device and/or stent, or the measured diameter of the body conduit, or a diameter that is slightly larger than the measured diameter of the body conduit. As used herein, "intermediate expanded configuration" refers to a configuration of the expandable device and/or stent in between the collapsed configuration and the fully expanded configuration. When the expandable device and/or stent is described in a "laid flat" configuration, it should be assumed that the expandable device and/or stent is in a relaxed state, i.e., is not under any compressive or tensile forces, nor any forces that would cause the spines of the expandable device and/or stent to move away from one another.

As used herein, the term "longitudinal" refers to a direction along an axis that extends through the lumen of the expandable device and/or stent while in a tubular configuration, and the term "circumferential" can refer to a direction within a plane that is orthogonal to the longitudinal axis and extends around the circumference of the device when in a tubular configuration.

As used herein, the terms "generally," "substantially," "about," and similar terms are used as terms of approximation and not as terms of degree, and are intended to account for the inherent variations in measured or calculated values that would be recognized by those of ordinary skill in the art.

As used herein, "body conduit" and "blood flow passage" refer to any anatomical structure through which blood or other bodily fluids regularly flow, such as a native annulus (in the heart or anywhere in the vasculature), a heart chamber, a blood vessel, a ureter, an esophagus, a biliary tract, and others.

II. Expandable Devices of the Present Technology

Figure 1A:
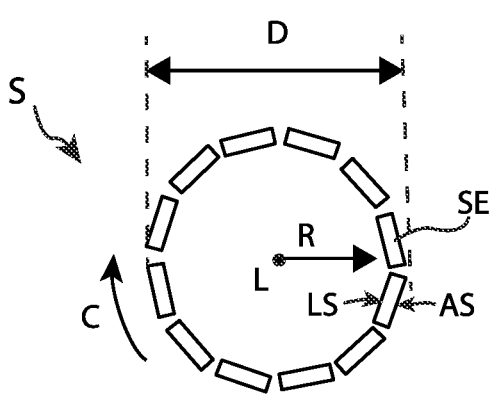
FIG. 1A is a cross-sectional end view of a prior art stent.
Figure 1B:
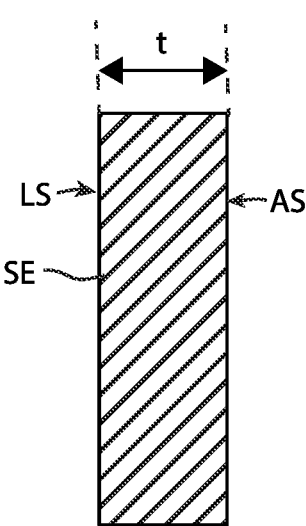
FIG. 1B is a cross-sectional end view of a structural member of the prior art stent shown in FIG. 1A.
Figure 1C:
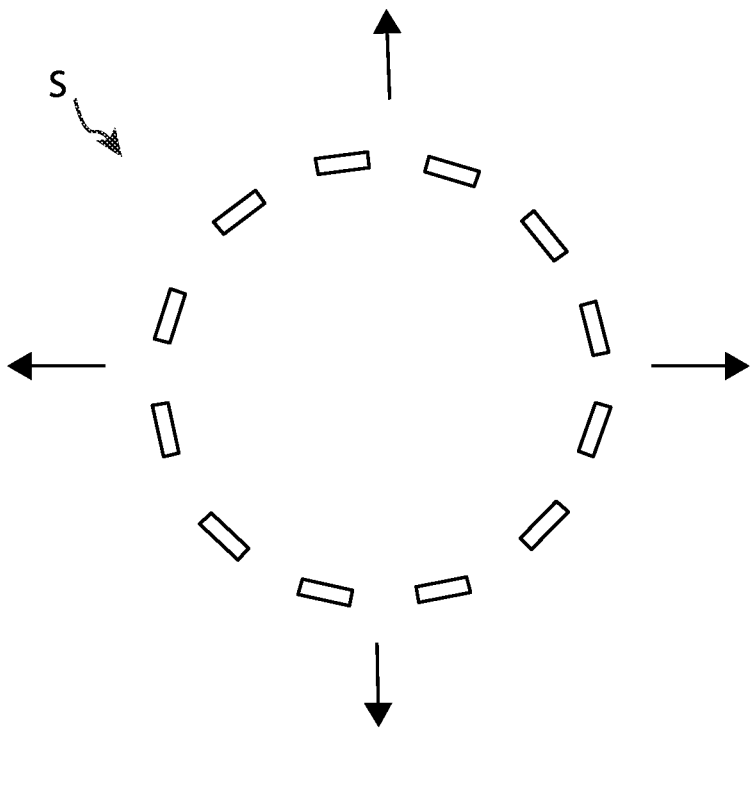
FIG. 1C is a cross-sectional end view of the prior art stent shown in FIG. 1A in an expanded configuration.

FIGS. 1A and 1C show an axial cross-sectional view of a conventional stent S in a collapsed configuration and an expanded configuration, respectively. The sidewall comprising the stent is formed of a plurality of interconnected structural elements SE (such as struts). As shown in the enlarged, isolated cross-section of one of the structural elements SE in FIG. 1B, the sidewall of the stent has a thickness t measured along a radial dimension R between an abluminal surface AS of the structural elements defining the sidewall and a luminal surface LS of the structural elements defining the sidewall. As stents are typically cut from a sheet or tube of material having a constant thickness, the thickness of most existing stents is also generally constant, both along the length of the stent and around the circumference. The structural members forming the stent wall flex either plastically (with a balloon-expandable stent) or elastically (with a self-expanding stent) so that the overall diameter of the stent increases. However, stents are typically designed to expand in diameter such that the wall thickness remains constant during expansion, and such that the structural members defining the wall remain generally radially aligned within a cylindrical surface. A stent cut from a tubing with a wall thickness of 0.010 inches will still have a wall thickness of 0.010 inches when it is radially expanded to a larger diameter. The larger diameter is created exclusively by the increasing arc length between the structural members of the stent as it expands.

According to several aspects of the technology, the expandable devices disclosed herein comprise a stent formed of a tubular sidewall configured to be positioned within a body conduit, such as a blood flow passage. Radial expansion of the stent causes portions of the sidewall to buckle out of the cylindrical surface defined by the non-buckling portions of the sidewall. The buckled portions thus form a plurality of bumps or arched protrusions extending radially inwardly and/or outwardly from the stent wall, which provide the stent with several benefits over existing devices. For example, the buckled portions can create an annular flow region around the main lumen of the stent that provides an alternative blood flow passage when an occlusive member (such as a balloon) is expanded within and occluding the main lumen. The buckled portions may separate the main lumen/expanded balloon and the surrounding tissue while simultaneously transferring the radially outward force generated by the balloon to the tissue. In these and other applications, the buckled portions may serve as frictional elements that engage apposing tissue at the treatment site (such as a blood vessel wall or a native valve leaflet) to secure the expandable device at a desired location and limit migration. These and other applications of the present technology and the attendant advantages will be discussed in greater detail herein.

Figures 2A, 2B:
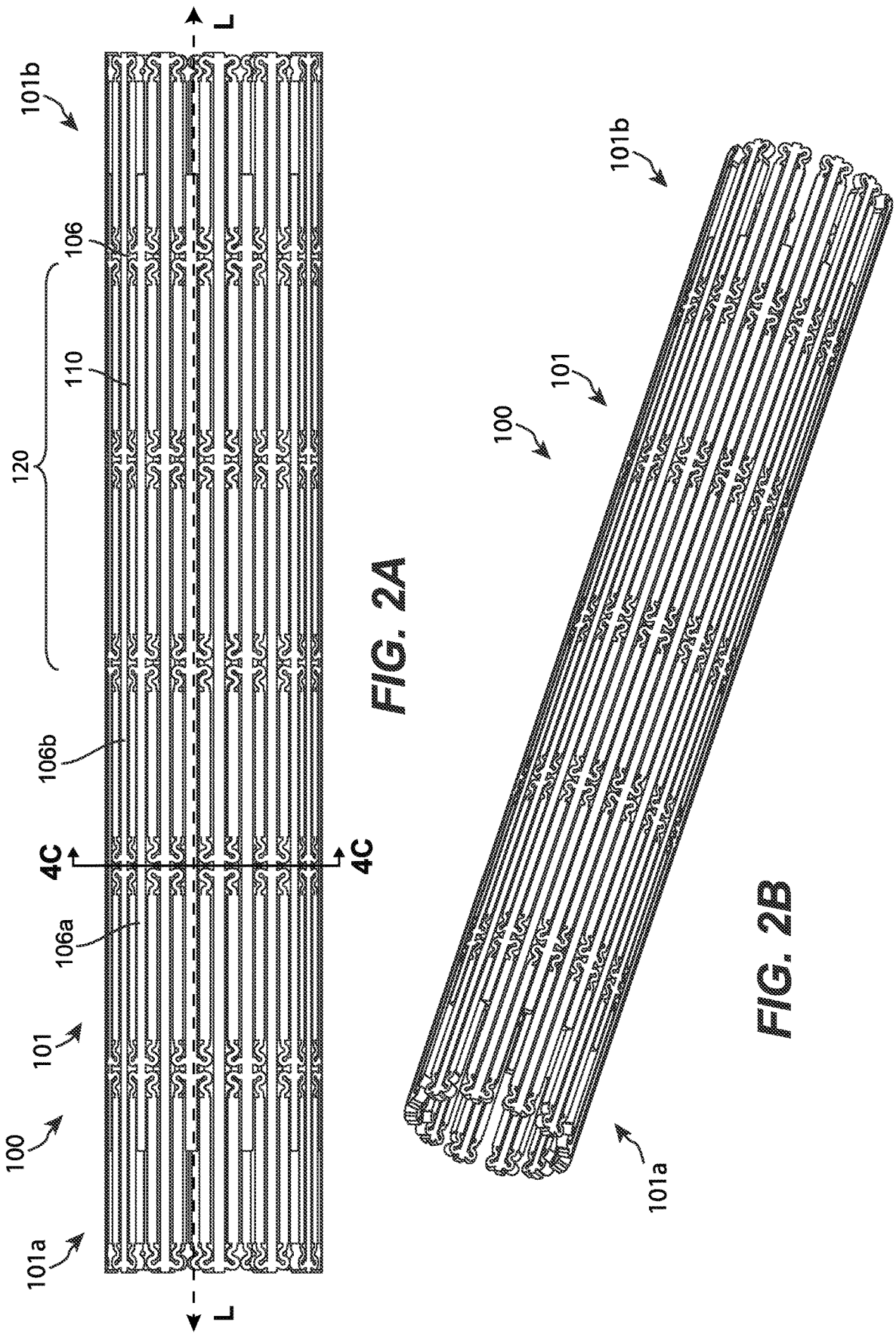
FIG. 2A is a side view of an expandable device in a tubular configuration configured in accordance with embodiments of the present technology.
FIG. 2B is an isometric view of the expandable device shown in FIG. 2A.
Figure 2C:
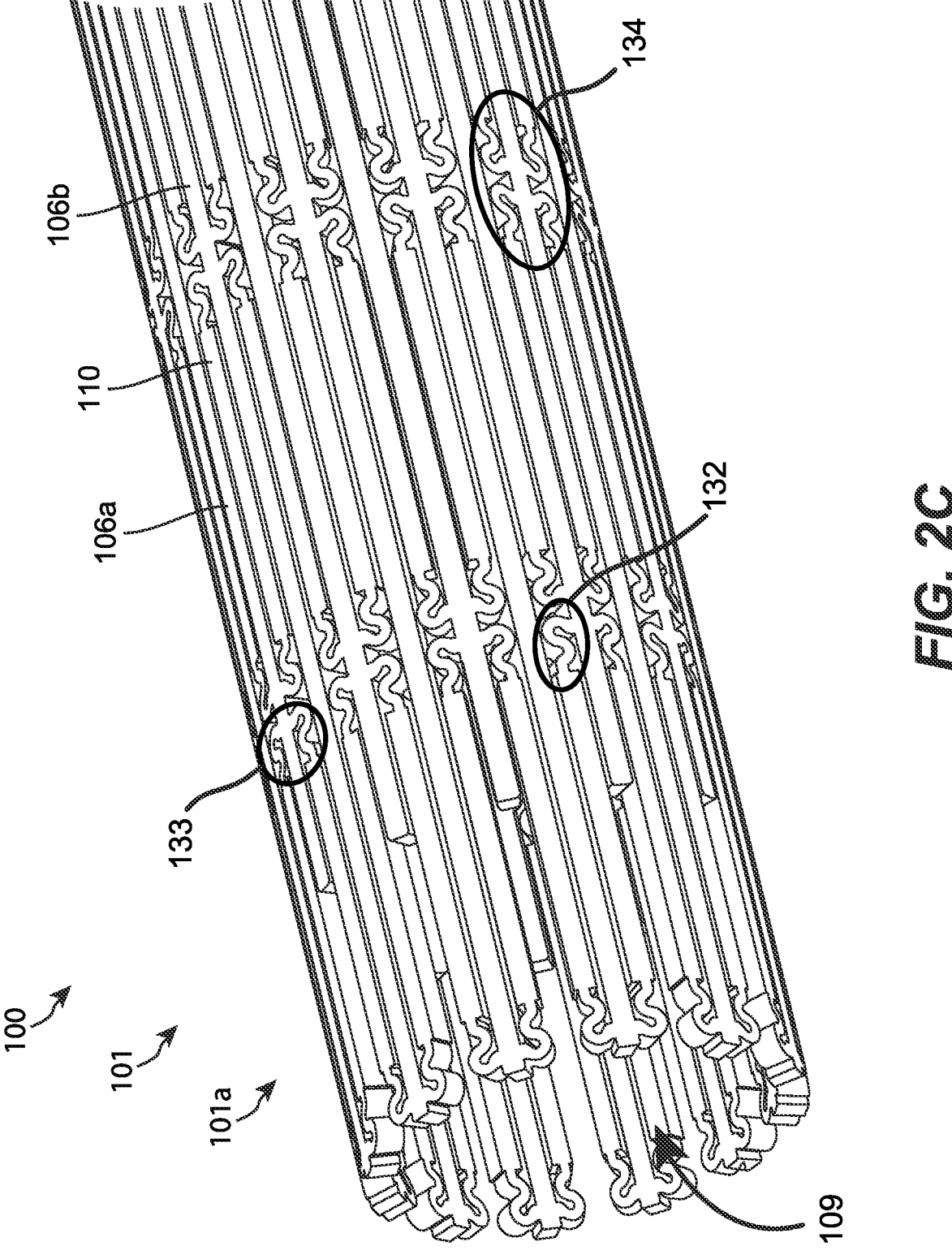
FIG. 2C is an enlarged, isometric view of a portion of the expandable device shown in FIGS. 2A and 2B.
Figure 2D:
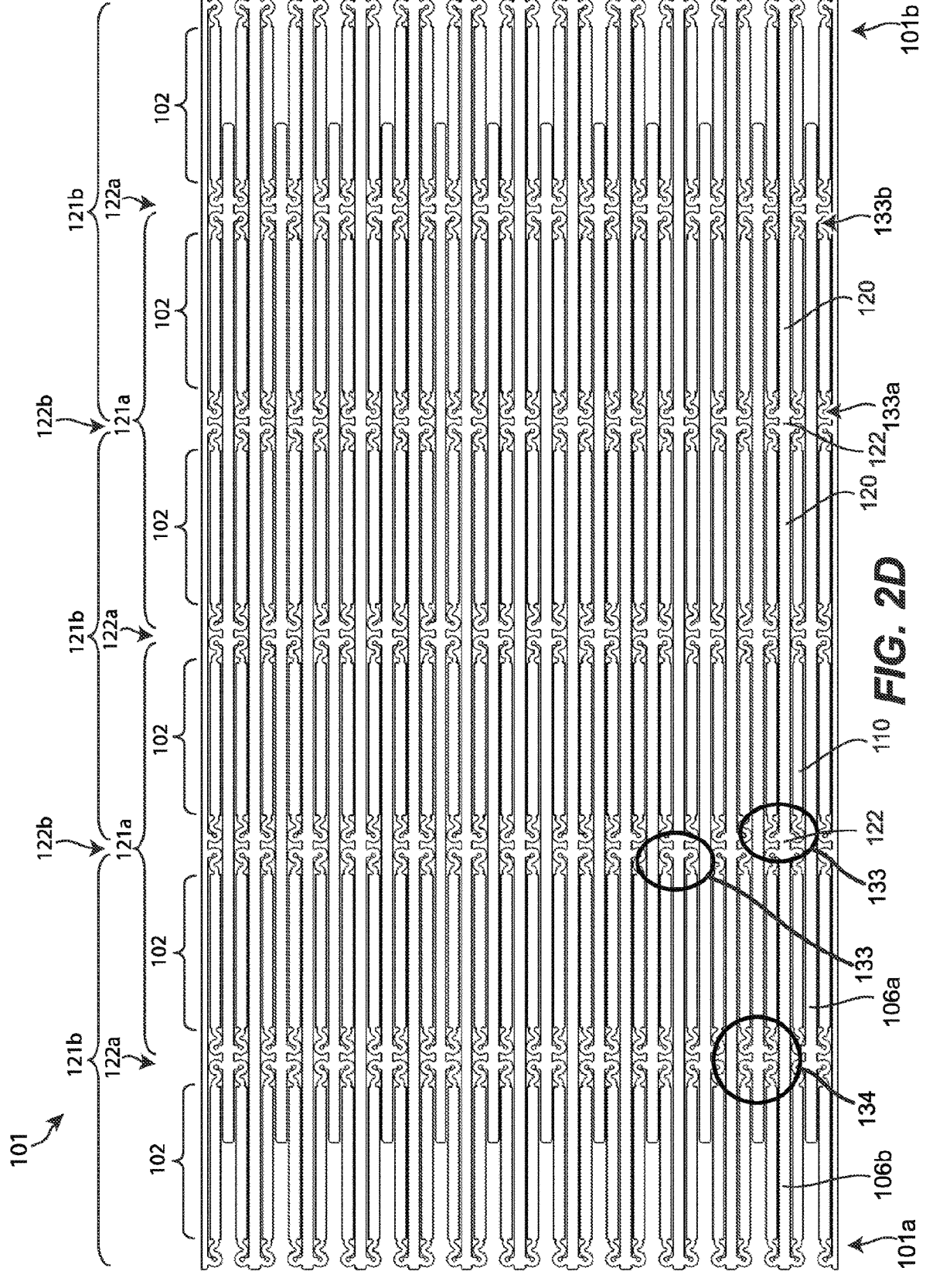
FIG. 2D is an elevation view of the expandable device shown in FIGS. 2A-2C in a laid flat configuration.

FIGS. 2A-2D illustrate an expandable device 100 configured in accordance with several embodiments of the present technology. FIGS. 2A-2C show the expandable device 100 in a collapsed (i.e., unexpanded), tubular configuration, and FIG. 2D shows the expandable device 100 as it would appear if, while in the collapsed configuration, it was cut longitudinally and then laid flat. The expandable device 100 is configured to be delivered in the collapsed, tubular configuration to a treatment site within a body conduit, such as a blood flow passage, and radially expanded at the treatment site to treat or facilitate treatment of the body conduit. The expandable device 100 may comprise a stent 101 having a first end portion 101a, a second end portion 101b, and a length extending between the first and second end portions 101a, 101b along a longitudinal axis L (see FIG. 2A) of the stent 101. The stent 101 may comprise a tubular sidewall formed of a plurality of longitudinally-extending spines 106 and a plurality of struts 110 extending between circumferentially adjacent spines 106. As detailed herein, the spines 106 may include one or more first portions 120 configured to bow outwardly from the sidewall of the stent 101 when the expandable device 100 is in an expanded configuration.

According to some embodiments, for example as shown in FIGS. 2A-2D, each of the spines 106 may be connected to an adjacent spine 106 via one or more of the struts 110. For example, each of the struts 110 can have a first end portion coupled to a first one of the spines 106 and a second end portion coupled to a second one of the spines 106. As such, some or all of the struts 110 may extend between spines 106 and may not directly connect to another strut 110. In some embodiments, some or all of the struts 110 may extend between circumferentially adjacent spines 106 such that the spines and struts alternate about a circumference of the stent.

The end portions of the struts 110 may be coupled to the spines 106 via joints 132. The joints 132 may correspond to the first and second end portions of the struts 110, or may extend from the first and second end portions of the struts 110. The joints 132 can have a width, thickness, and shape designed to allow the struts 110 to swing away from the adjacent spines 106 as the device 100 radially expands, as well as to withstand the tension exerted on the struts 110 by the spines 106 as the spines 106 move away from one another during expansion. In some embodiments, the stent 101 can include one or more spines 106 that are not connected to another spine 106 by a strut 110 and/or one or more spines 106 that are not connected to a strut 110.

According to some embodiments, for example as shown in FIGS. 2A-2D, some of the spines 106 may span only a portion of the length of the stent 101, while the other spines 106 may span the entire length of the stent 101. Likewise, one, some, or all of the spines 106 may have the same length, and one, some, or all of the spines 106 may have different lengths. As depicted, the stent 101 may include first spines 106a and second spines 106b that alternate about the circumference of the stent 101, where the first spines 106a are shorter than the second spines 106b. In some embodiments, the first and second spines 106a, 106b have the same length.

In some embodiments, the first end of one, some, or all of the struts 110 is coupled to one of the first spines 106a, and the second end of the strut(s) 110 may be coupled to one of the second spines 106b. The longer second spines 106b may extend longitudinally beyond one or both longitudinal ends of the first spines 106a, as shown, or a longitudinal end of the second spines 106b may be aligned with a longitudinal end of the first spines 106a. In some embodiments, no first spine 106a is circumferentially adjacent another first spine 106a and no second spine 106b is circumferentially adjacent another second spine 106b. In some embodiments, two or more first spines 106a may be circumferentially adjacent and/or two or more second spines 106b may be circumferentially adjacent.

At least when the stent is represented in a laid-flat view, for example as shown in FIG. 2D, one, some, or all of the spines 106 may be generally linear and substantially parallel to: (a) the longitudinal axis L of the stent 101, (b) one, some, or all of the struts 110, and/or (c) one, some, or all of the other spines 106. In these and other embodiments, when the stent 101 is in the collapsed configuration, one, some, or all of the spines 106 may be generally linear and substantially parallel to: (a) the longitudinal axis L, (b) one, some, or all of the struts 110, and/or (c) one, some, or all of the other spines 106.

Some or all of the struts 110 may be generally linear, as shown in FIGS. 2A-2D. At least when the stent is represented in a laid-flat view, for example as shown in FIG. 2D, the struts 110 may be generally linear and substantially parallel to: (a) the longitudinal axis L, (b) one, some, or all of the spines 106, and/or (c) the other struts 110 within the same strut region 102 and/or some or all of the other strut regions. In these and other embodiments, when the stent 101 is in the collapsed configuration, the struts 110 may be generally linear and substantially parallel to: (a) the longitudinal axis L, (b) one, some, or all of the spines 106, and/or (c) the other struts 110 within the same strut region 102 and/or some or all of the other strut regions. According to some embodiments, the struts 110 may be generally linear and angled relative to the longitudinal axis L and/or angled with respect to one, some, or all of the spines 106 when the stent is in an expanded configuration. In some embodiments, all or a portion of one or more of the struts 110 may be curved when the stent 101 is in a collapsed configuration and/or when the stent 101 is in an expanded configuration.

As best shown in FIG. 2D, the stent 101 may comprise a plurality of strut regions 102, each comprising a circumferential band of struts 110 within which adjacent struts 110 are separated by a coextending length of a spine 106. Each of the strut regions 102 may be longitudinally disposed between the first and second end portions of the struts 110 within the region 102 (and, similarly, between the joints 132 at the end portions of the struts 110 within the region 102). At least when the stent 101 is in a collapsed configuration, the first end portions of the struts 110 within a given strut region 102 may be longitudinally aligned with one another and the second end portions of the struts 110 within a given strut region 102 may be longitudinally aligned with one another.

According to some embodiments, a first longitudinal side of each of the strut regions 102 may be defined by a circumferential band composed of first pairs 133a of joints 132 facing towards the second end portion 101b of the stent 101 (i.e., the struts 110 attached to the joints 132 of the first pairs 133a form a V-shape that opens in the direction of the second end portion 101b), and a second longitudinal side of each of the strut regions 102 may be defined by a circumferential band composed of second pairs 133b of joints 132 facing towards the first end portion 101a of the stent 101 (i.e., the struts 110 attached to the joints 132 of the second pairs 133b form a V-shape that opens in the direction of the first end portion 101a). The first pairs 133a of joints may be disposed along the first spines 106a and the second pairs 133b of joints may be disposed along the second spines 106b.

The strut regions 102 may be longitudinally adjacent one another along the length of the stent 101 such that the band of first pairs 133a of joints 132 of a first one of the strut regions 102 may be longitudinally adjacent the band of second pairs 133b of joints 132 of a longitudinally adjacent second strut region 102. The spines 106 may extend longitudinally across two or more strut regions 102, and thus at least some of the first pairs 133a are coupled to the second pairs 133b via a second portion 122 (described below) of the respective spine 106 along which the pairs 133a, 133b are disposed. First and second pairs 133a, 133b of joints that are longitudinally adjacent and radially aligned may comprise nodes 134.

According to some embodiments, for example as shown in FIG. 2D, one, some, or all of the spines 106 may comprise first portions 120 and second portions 122 that alternate along the lengths of the respective spines 106. Only a few of the first portions 120 and second portions 122 are labeled in FIG. 2D for ease of viewing the structure of the stent. First and second end portions 120a and 120b (see FIG. 3C) of the first portions 120 may be coupled to and continuous with one of the second portions 122. The first portions 120 may span one, two, or more strut regions 102, and the second portions 122 may extend between longitudinally adjacent strut regions 102 and between longitudinally adjacent first portions 120. In some embodiments, for example as shown in FIG. 2D, the first portions 120a of the first spines 106a are longitudinally staggered relative to the first portions 120b of the second spines 106b such that the first portions 120a of the first spines 106a and the first portions 120b of the second spines 106b are coextensive along only a portion of their respective lengths.

As best shown in FIG. 2D, the stent 101 may comprise a plurality of spine regions 121, each comprising a circumferential band of circumferentially adjacent first portions 120 and the four struts 110 coupled to each of the first portions 120. Each of the spine regions 121 may be longitudinally disposed between second end portions 122 on either side of the respective first portions 120. In those embodiments where the stent 101 comprises first and second spines 106a, 106b, the stent 101 may comprise first spine regions 121a along the first spines 106a and second spine regions 106b along the second spines 106b. The first portions 120 within the first spine regions 121a may be generally circumferentially aligned and the first portions 120 within the second spine regions 121b may be generally circumferentially aligned, while the first portions 120 in the first spines regions 121a and the first portions 120 in the second spine regions 121b may be circumferentially offset.

The stent 101 may comprise different numbers of first and second spine regions 121a, 121b. For example, in the embodiments represented by FIG. 2D, the stent 101 comprises three first spine regions 121a and two second spine regions 121b. In other embodiments, the stent 101 may comprise more or fewer first spine regions 121a and/or more or fewer second spine regions 121b. In the embodiments represented by FIG. 2D, each of the spine regions 121 comprise 12 first portions 120 and 48 struts 110, and the stent 101 is approximately 25 mm long with 60 total first portions 120 and 144 total struts 110. In other embodiments, the stent 101 may be longer or shorter and/or comprise more or fewer than 12 first portions 120 per spine region 121 (e.g., 1, 2, 3, 4, 5, 6, 7, 8, 9, 10, 11, 13, 14, 15, 16, 17, 18, 19, 20, 22, 23, 24, etc. first portions 120 per spine region 121), one or more buckled portions 150 (see FIGS. 3A and 3B) within a given spine region 121 and/or first portion 120, more or fewer than 48 struts 110 per spine region 121 (e.g., 0, 2, 4, 6, 8, 10, 12, 14, 16, 18, 20, 22, 24, 26, 28, 30, 32, 36, 40, 44, 52, 56, 60, 64, 68, 72, 76, 80, etc. struts 110 per spine region 121), more or fewer than 60 total first portions 120, and/or more or fewer than 144 total struts 110. The first and second spine regions 121 may have the same or different numbers of first portions 120 and/or struts 110. Within one, some, non, or all of the spine regions 121, the strut 110 to first portion 120 ratio may be 2 to 1, 3 to 1, 4 to 1, 5 to 1, 6 to 1, 7 to 1, 8 to 1, and others.

The first and second spine regions 121a, 121b may overlap along the longitudinal axis of the stent 101 (as shown in FIG. 2D), or the first and second spine regions 121a, 121b may be longitudinally adjacent one another, or spaced apart. In some embodiments, the stent 101 includes some overlapping spine regions 121 and some adjacent or spaced apart spine regions 121. The spine regions 121 may overlap, for example, by the length of a strut region 102 such that longitudinally overlapping spine regions 121 share a strut region 102.

Figure 3A:
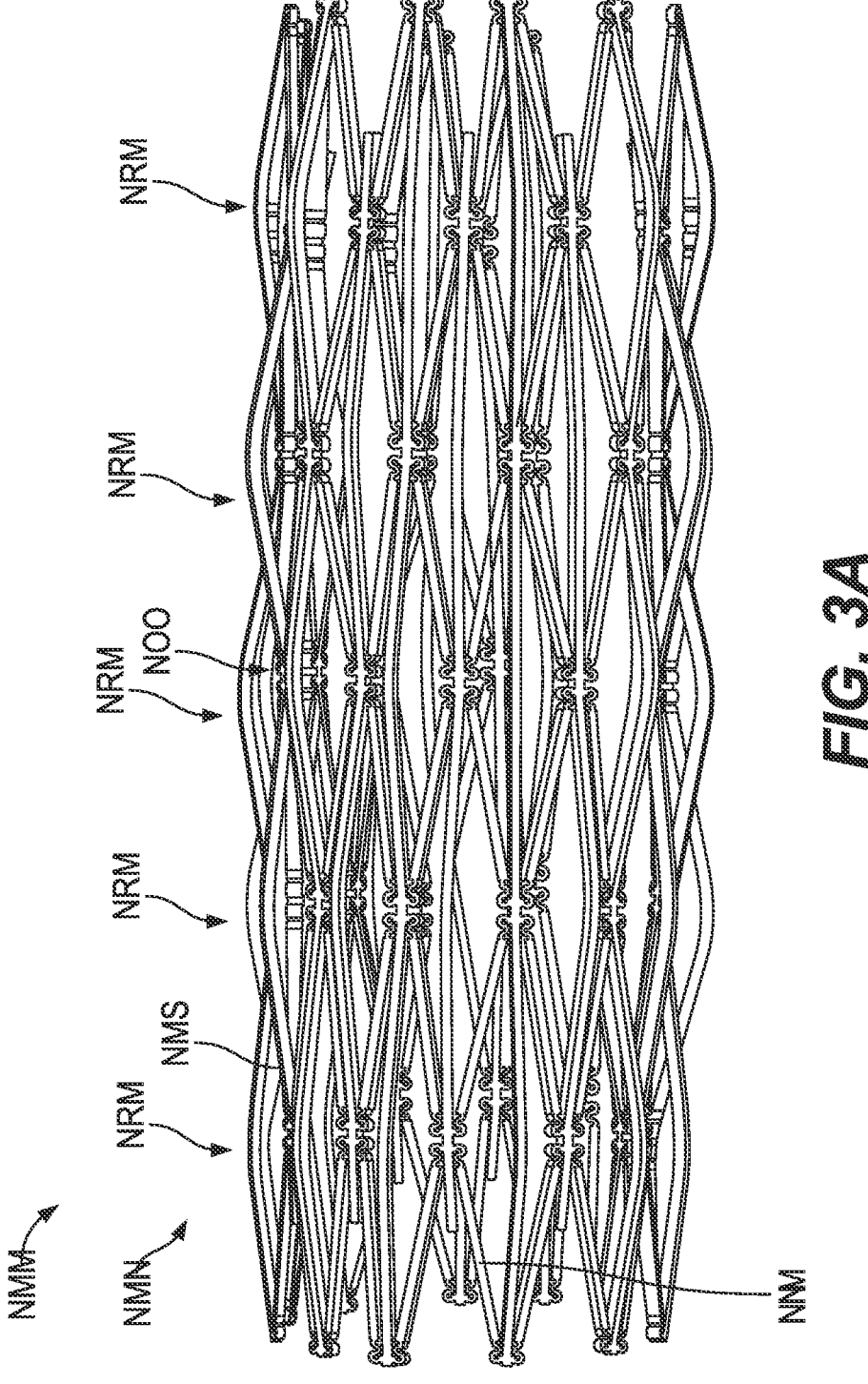
FIG. 3A is a side view of the expandable device shown in FIGS. 2A-2D in an intermediate expanded configuration in accordance with embodiments of the present technology.
Figure 3B:
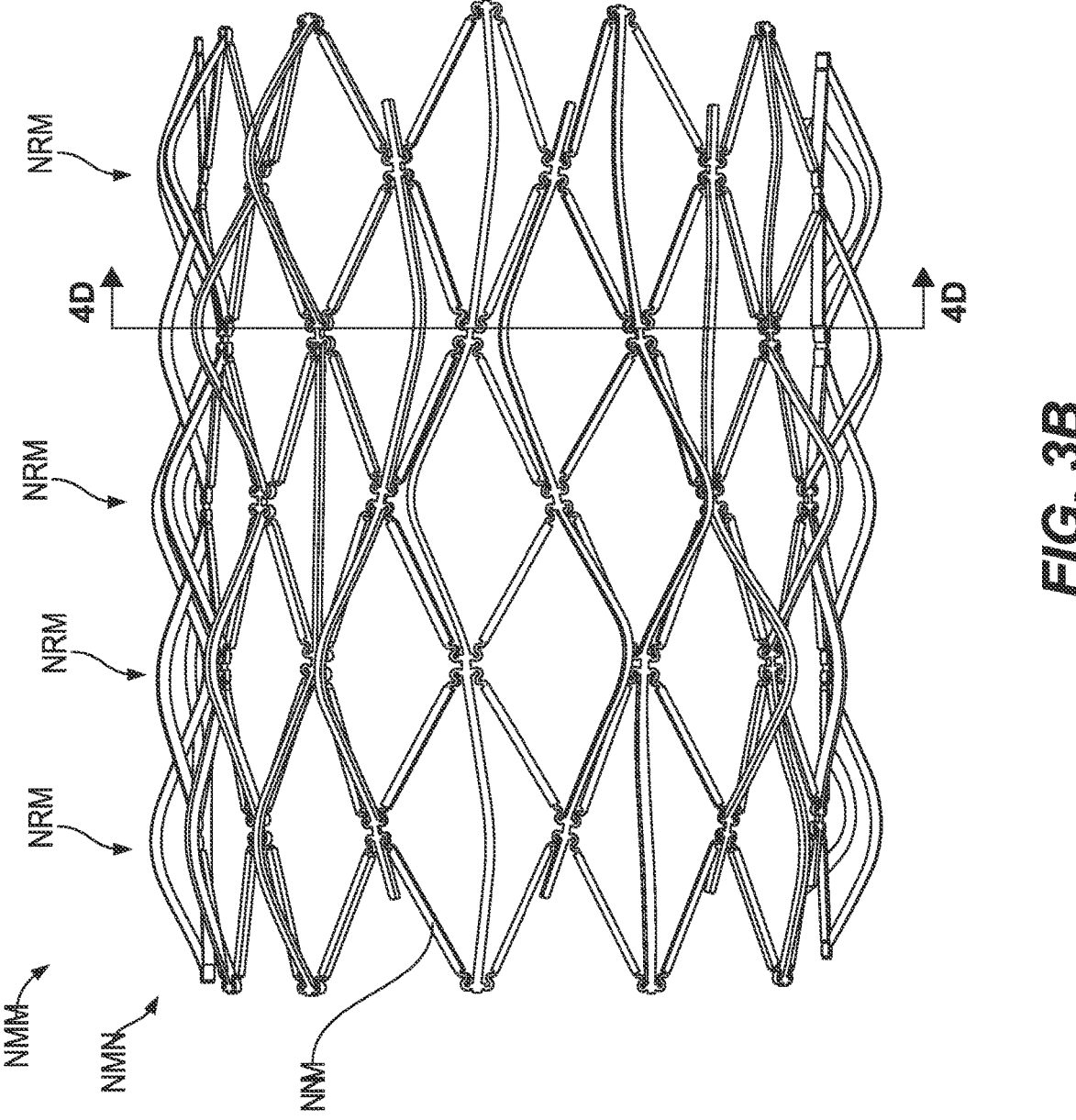
FIG. 3B is a side view of the expandable device shown in FIGS. 2A-2D in a fully expanded configuration in accordance with embodiments of the present technology.
Figure 3C:
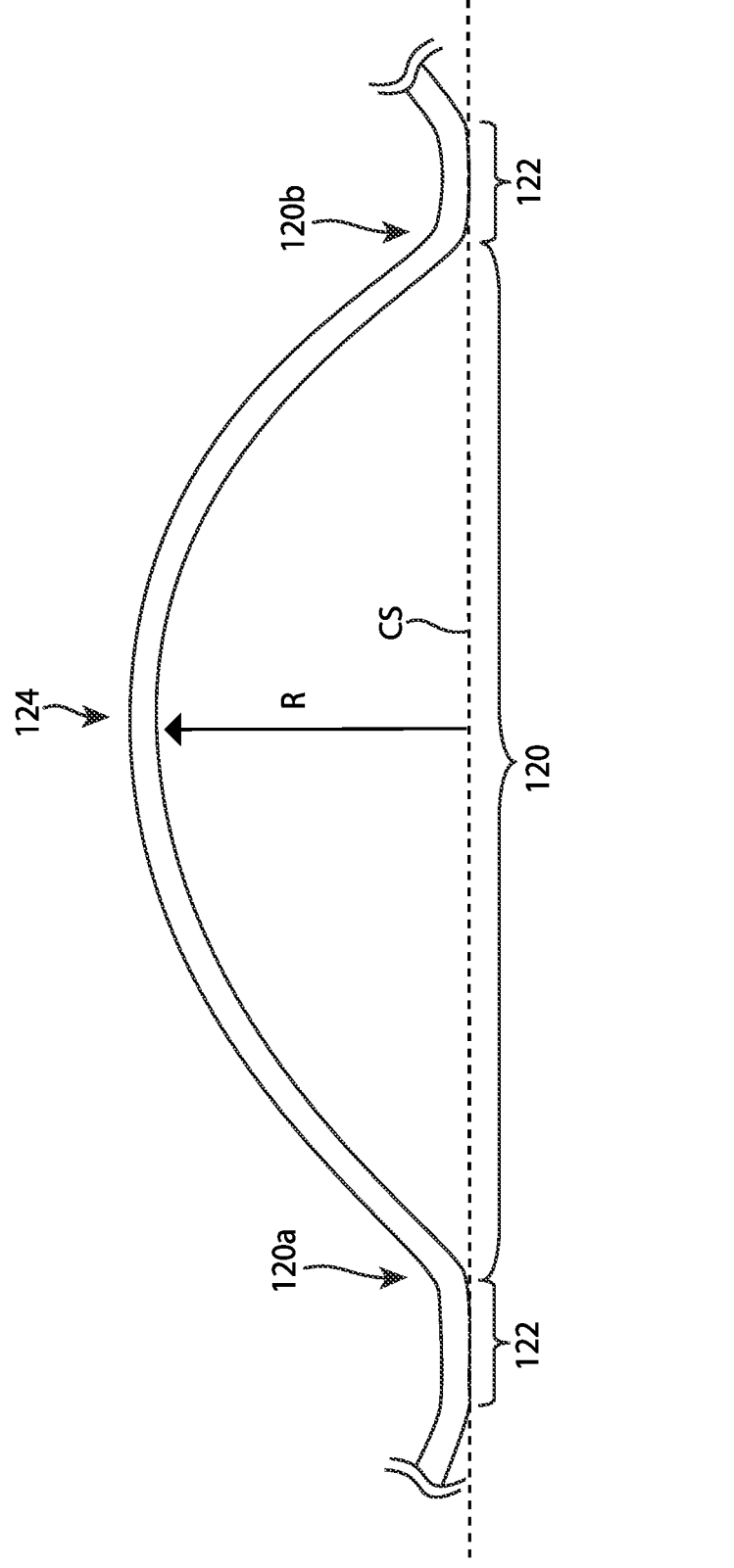
FIG. 3C is a side view of a portion of a spine configured in accordance with the present technology, shown isolated from an expandable device in an expanded configuration.

FIGS. 3A and 3B are side views of the stent 101 in an intermediate expanded configuration and a fully expanded configuration, respectively, and FIG. 3C is a side view of one of the first portions 120 of the spines 106 when the stent 101 is in the fully expanded configuration. According to some embodiments, for example as depicted in FIGS. 3A-3C, transformation of the stent 101 from the collapsed configuration to the expanded configuration causes the first portions 120 to bow out of a substantially cylindrical surface CS defined by the second portions 122 such that, at least in the expanded configuration, the first portions 120 form a plurality of buckled portions 150 extending radially away from the rest of the sidewall. The buckled portions 150, for example, may be disposed along one or more of the spines 106 and may be spaced apart about a length and/or circumference of the stent 101.

In some embodiments, for example as shown in FIGS. 3A-3C, the buckled portions 150 comprise arched regions of the respective spine 106. The buckled portions 150 can have a peak region 124 between the first and second end portions 120a, 120b, where the peak region 124 comprises a location or region of the buckled portion 150 that is radially farthest from the second portions 122. As discussed herein, a radial distance R measured between (a) the cylindrical surface CS defined by the plurality of second portions 122 and (b) the peak regions 124 of the buckled portions 150 defines a thickness of the annular lumen created by the buckled portions 150.

Each of the buckled portions 150 may span two strut regions 102, as shown in FIG. 2D. In some embodiments, one, some, or all of the buckled portions 150 span more than two strut regions 102 (e.g., three strut regions, four strut regions, etc.). The first spines 106a may have fewer buckled portions 150 than the second spines 106b, or vice versa. In some embodiments, the first and second spines 106a, 106b have the same number of buckled portions 150. One, some, none, or all of the spines 106 may have a single buckled portion 150. The length of the buckled portions 150 along a given spine 106 may be the same or may vary, and the length of the second portions 122 along a given spine 106 may be the same or vary. Additionally or alternatively, the buckled portions 150 of some or all of the spines 106 may have different lengths.

Figures 4A, 4B:
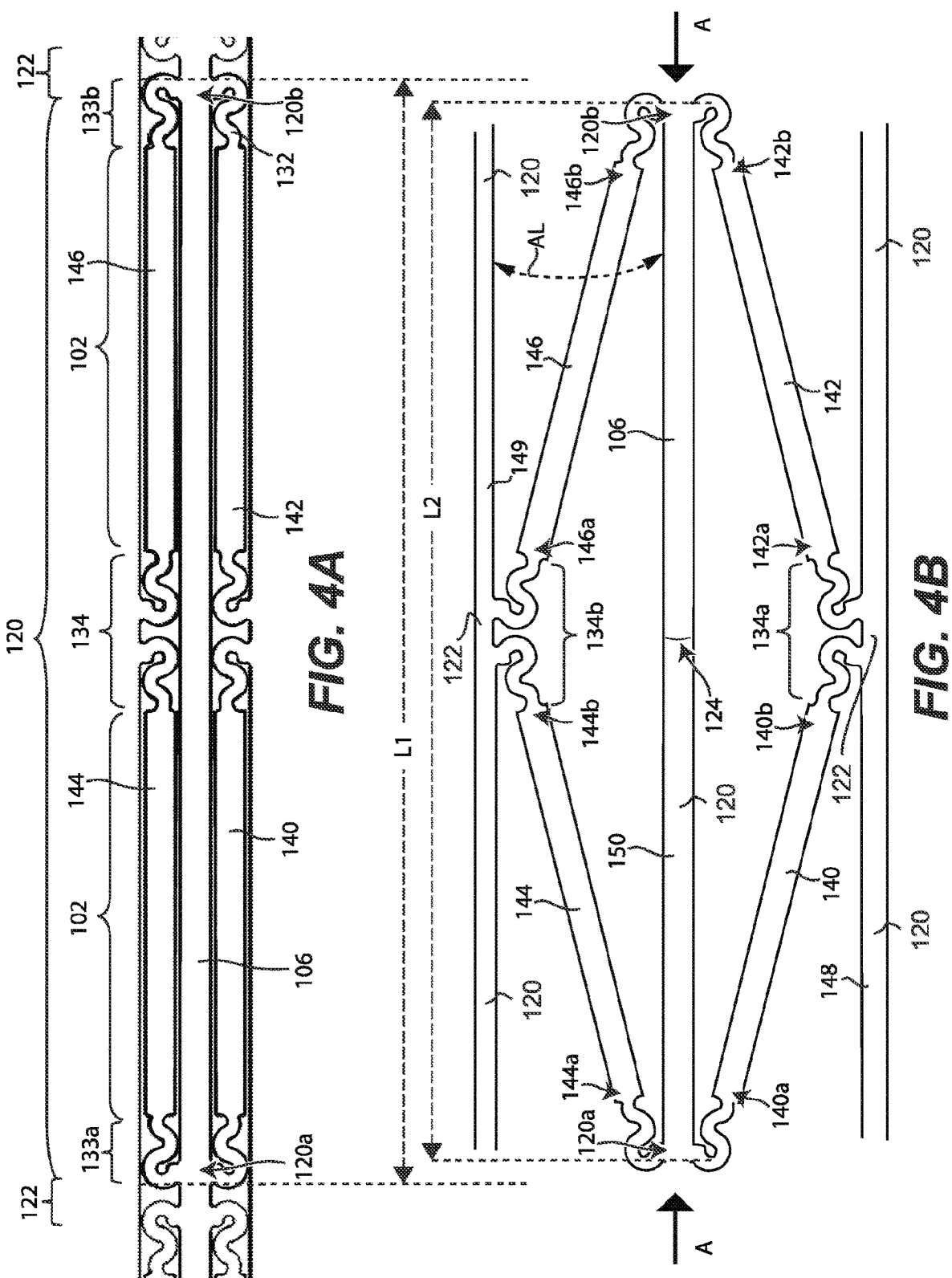
FIG. 4A is an enlarged portion of an expandable device configured in accordance with several embodiments of the present technology, shown in a collapsed configuration.
FIG. 4B is an enlarged portion of an expandable device configured in accordance with several embodiments of the present technology, shown in an expanded configuration.
Figure 4C:
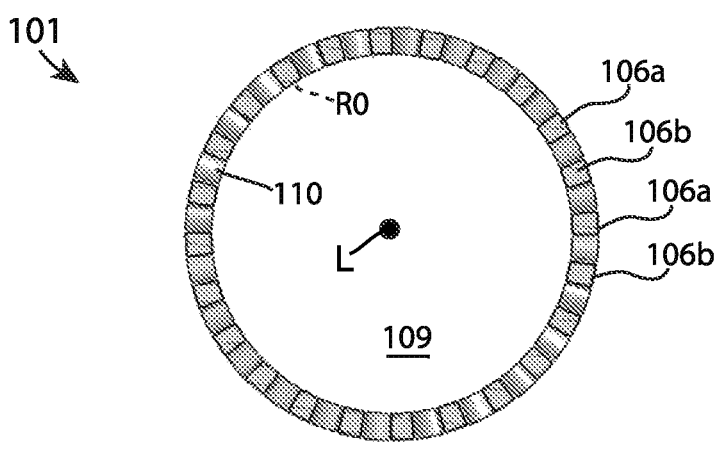
FIG. 4C is an axial cross-sectional view of the expandable device in a collapsed configuration, as shown in FIG. 2A, taken along line 4C-4C.
Figure 4D:
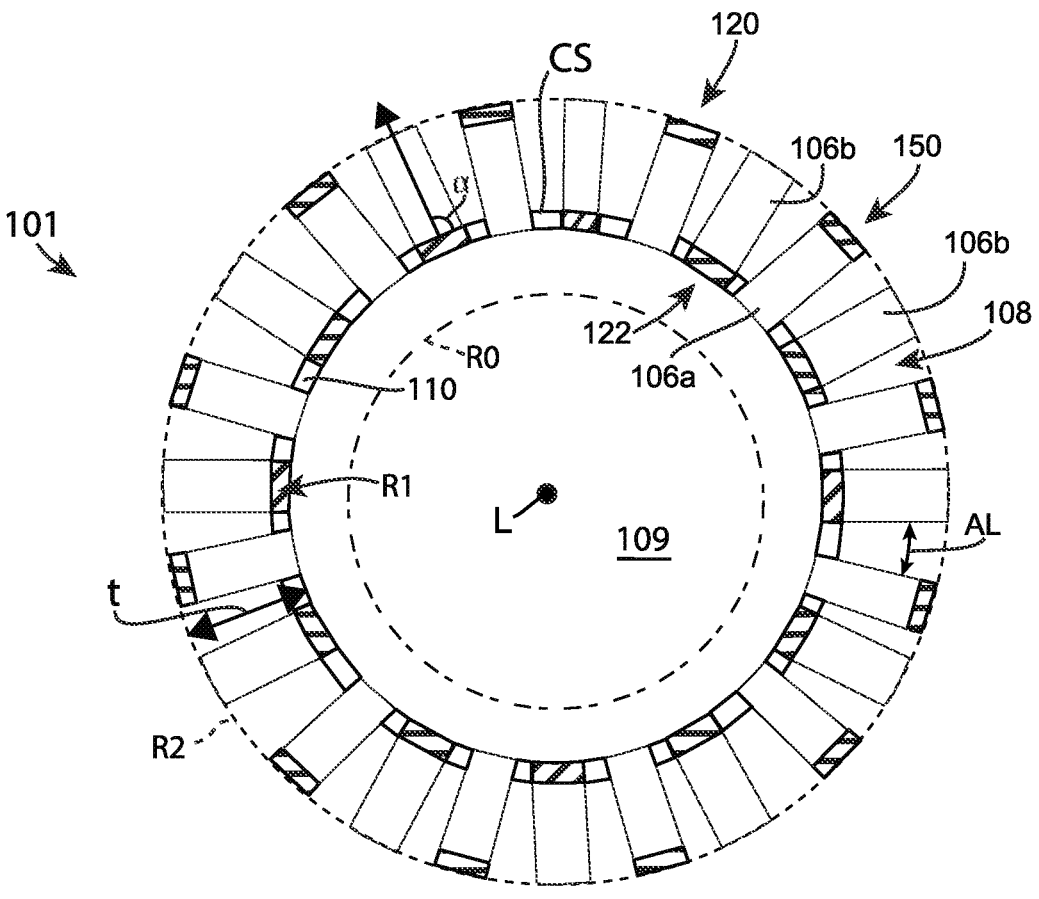
FIG. 4D is an axial cross-sectional view of the expandable device in an expanded configuration, as shown in FIG. 3B, taken along line 4D-4D.

According to some embodiments, movement of the struts 110 during radial expansion of the stent 101 may axially compress portions of the spines 106, thereby causing the first portions 120 to bow away from the cylindrical surface CS and form the buckled portions 150. For example, FIGS. 4A and 4C depict a portion of the stent 101 in a collapsed configuration, and FIGS. 4B and 4D show a portion of the stent 101 in an expanded configuration. The portion shown in FIGS. 4A and 4C includes a first portion 120 of one of the spines 106 and second portions 122 at either longitudinal end of the first portion 120, as well as first, second, third and fourth struts 140, 142, 144, and 146 coupled to the first portion 120 of the spine 106 via joints 132 at the first and second pairs of joints 133a, 133b. At least in the collapsed configuration, the first and second end portions 120a, 120b of the first portion 120 may be separated along the longitudinal axis of the stent 101 by a first length L1, and circumferentially adjacent spines 148, 149 may be separated from the spine 106 by an arc length AL. Also in the collapsed configuration, as best shown in FIG. 4C, the struts 110 (including struts 140, 142, 144, 146) and the spines 106 may be substantially the same radial distance, R0, from a central longitudinal axis L of the stent 101 and together define a main lumen 109.

In the enlarged portion of the stent 101 shown in FIGS. 4A and 4B, a first end portion 140a of the first strut 140 is connected to a first end portion 120a of the first portion 120 of the spine 106, and a second end portion 140b of the first strut 140 is connected to a second portion 122 of a first circumferentially adjacent spine 148 (only a portion shown) or other structural member of the sidewall. A first end portion 142a of the second strut 142 is connected to the second portion 122 of the first circumferentially adjacent spine 148 (only a portion shown) or other structural member of the sidewall, and a second end portion 142b of the second strut 142 is connected to a second end portion 120b of the first portion 120 of the spine 106. A first end portion 144a of the third strut 144 is connected to the first end portion 120a of the first portion 120 of the spine 106, and a second end portion 144b of the third strut 144 is connected to a second portion 122 of a second circumferentially adjacent spine 149 (only a portion shown) or other structural member of the sidewall. A first end portion 146a of the fourth strut 146 is connected to the second portion 122 of the second circumferentially adjacent spine 149 (only a portion shown) or other structural member of the sidewall, and a second end portion 146b of the fourth strut 146 is connected to the second end portion 120b of the first portion 120 of the spine 106.

Radial expansion of the stent 101 increases the radial distance between (a) the spines 106 and (b) the longitudinal axis L of the stent 101, which in turn increases an arc length AL between circumferentially adjacent spines 106. As the circumferential distance between the spines 106 increases, the struts 110 angle away from the spines 106 to which they are attached. For example, as shown in FIG. 4B, as the arc lengths AL between the spine 106 and the circumferentially adjacent spines 148, 149 increase, (a) the second end portion 140b of the first strut 140 and the first end portion 142a of the second strut 142 together move away from the spine 106 in a first circumferential direction (e.g., with node 134a), and (b) the second end portion 144b of the third strut 144 and the first end portion 146a of the fourth strut 146 move away from the spine 106 in a second circumferential direction (e.g., with node 134b) opposite the first circumferential direction. As a result, the end portions 140a and 142b, and 144a and 146b of the struts 140, 142, 144, 146 attached to the spine 106 are pulled longitudinally toward one another, and in so doing force the attached end portions 120a, 120b of the first portion 120 of the spine 106 along with them (indicated by arrows A in FIG. 4B). This movement longitudinally compresses the spine 106 so that a longitudinal distance between the first and second end portions 120a, 120b of the spine 106 decreases from the first length L1 in the collapsed configuration to a shorter second length L2. To accommodate this axial compression, the first portions 120 bow outwardly from the second portions 122 to form buckled portions 150. Accordingly, as best shown in FIG. 4D, when the stent 101 is in the expanded configuration, (a) the struts 110 and the second portions 122 of the spines 106 are a first radial distance R1 from the central longitudinal axis L, and (b) the first portions 120 of the spines 106 are a second, greater radial distance R2 from the central longitudinal axis L.

According to some embodiments, for example as shown in FIG. 4D, when the stent 101 is in the expanded configuration, the stent 101 defines two separate diameters which can be used to define two separate lumens. The stent 101 may have a first, main lumen 109 defined by the radially aligned struts 110 and the second portions 122 of the spines 106, and a second, annular lumen 108 between (a) the first portions 120 of the spines 106 and (b) the struts 110 and the second portions 122 of the spines 106. The annular lumen 108 may have a thickness t measured between (a) the first portions 120 of the spines 106 and (b) the struts 110 and the second portions 122 of the spines 106. The coaxial lumens of the expandable devices 100 and/or stents 101 of the present technology can be especially beneficial for applications requiring a balloon to be inflated within a blood flow passage that temporarily blocks blood flow through the passage. For example, the expandable device 100 and/or stent 101 may receive a balloon within the main lumen 109, and the balloon may be expanded within the main lumen 109, which also expands the stent 101. The annular lumen 108 created by the buckled portions 150 provides a blood flow passage through the body conduit while the balloon is expanded in the main lumen 109. Additional details and specific applications of this feature of the present technology are discussed elsewhere herein.

Figure 5A:
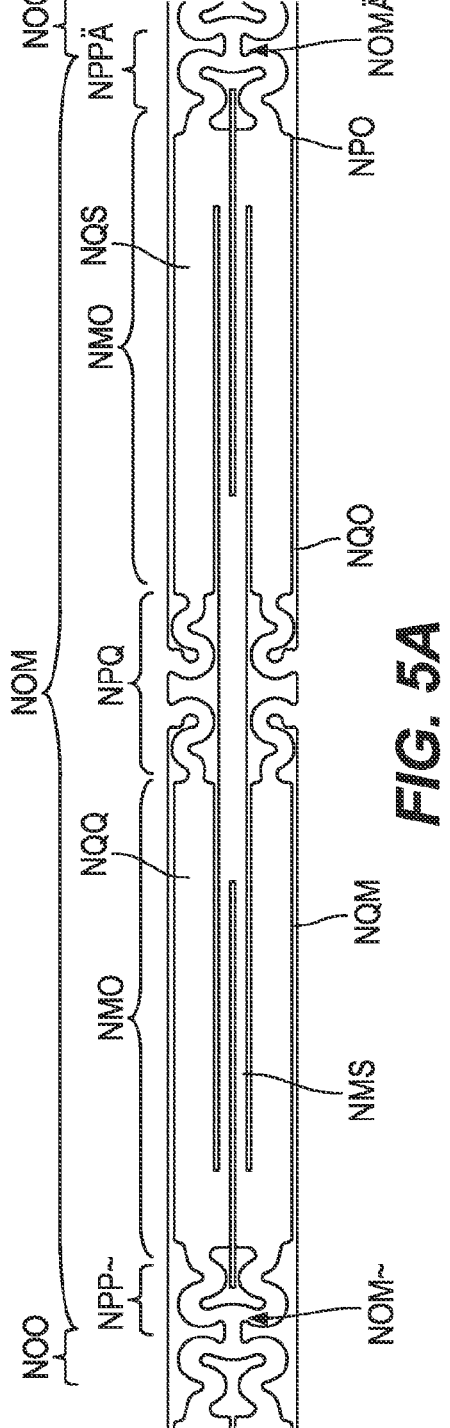
FIG. 5A is an enlarged portion of an expandable device configured in accordance with several embodiments of the present technology, shown in a collapsed configuration.
Figure 5B:
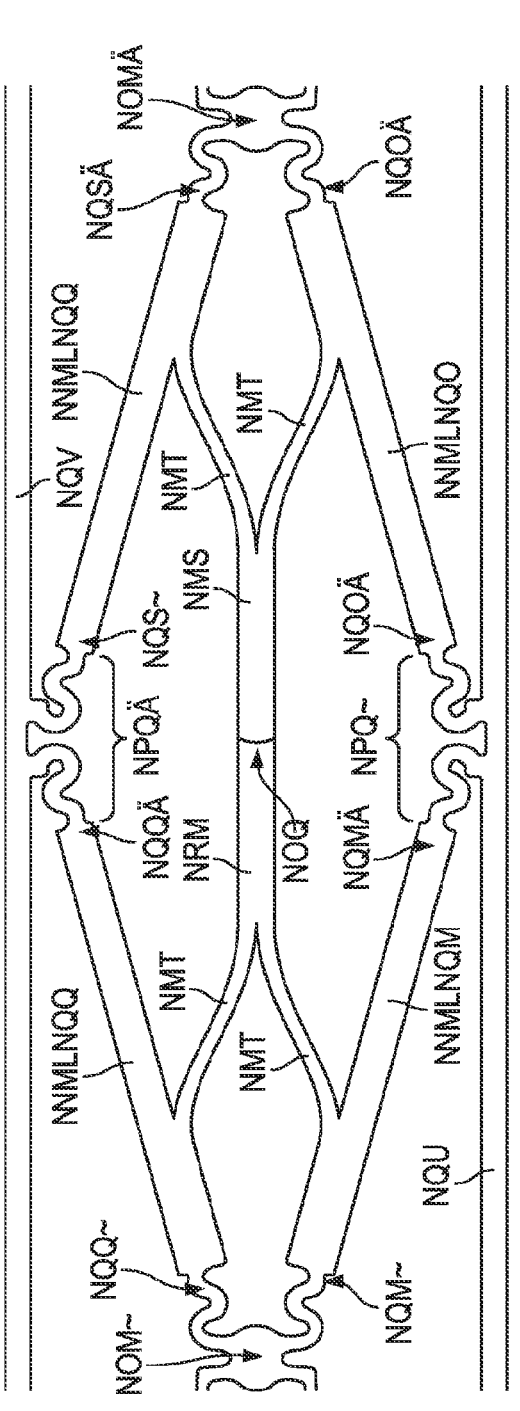
FIG. 5B is an enlarged portion of an expandable device configured in accordance with several embodiments of the present technology, shown in an expanded configuration.

According to some embodiments, for example as shown in FIG. 4D, the buckled portions 150 may extend radially away (outwardly or inwardly) from the substantially cylindrical surface CS at an angle a that is approximately 90 degrees. In some embodiments, one, some, or all of the buckled portions 150 may extend radially away from the substantially cylindrical surface CS as an angle other than 90 degrees (not shown). In some cases, however, it may be beneficial to ensure that one, some, or all of the buckled portions 150 extend radially away (outwardly or inwardly) from the substantially cylindrical surface CS at approximately 90 degrees. In such embodiments, it may be beneficial to configure the spines 106 and/or struts 110 to improve the directional stability and/or angular predictability of the buckled portions 150. For example, as shown in FIGS. 5A and 5B, in some embodiments one, some, or all of the first portions 120 of the spines 106 have end portions that connect directly to the struts 110 rather than to the second portions 122 or end pairs 133. The first portions 120 may branch into two legs 107 at one or both of its ends, and each of the legs 107 may connect to one of the struts 110. As a result, as the struts 110 expand circumferentially and the spines 106 start to buckle, the legs 107 establish a broader lateral support for the spines 106 and guide the buckled portions 150 into an orientation relative to the rest of the stent 101 that is substantially radially inward or outward. Additionally or alternatively, the first portions 120 of the stent 101 may be pre-formed (e.g., via heat treatment) to encourage the creation of buckled portions 150 of a desired orientation.

Figures 6A, 6B:
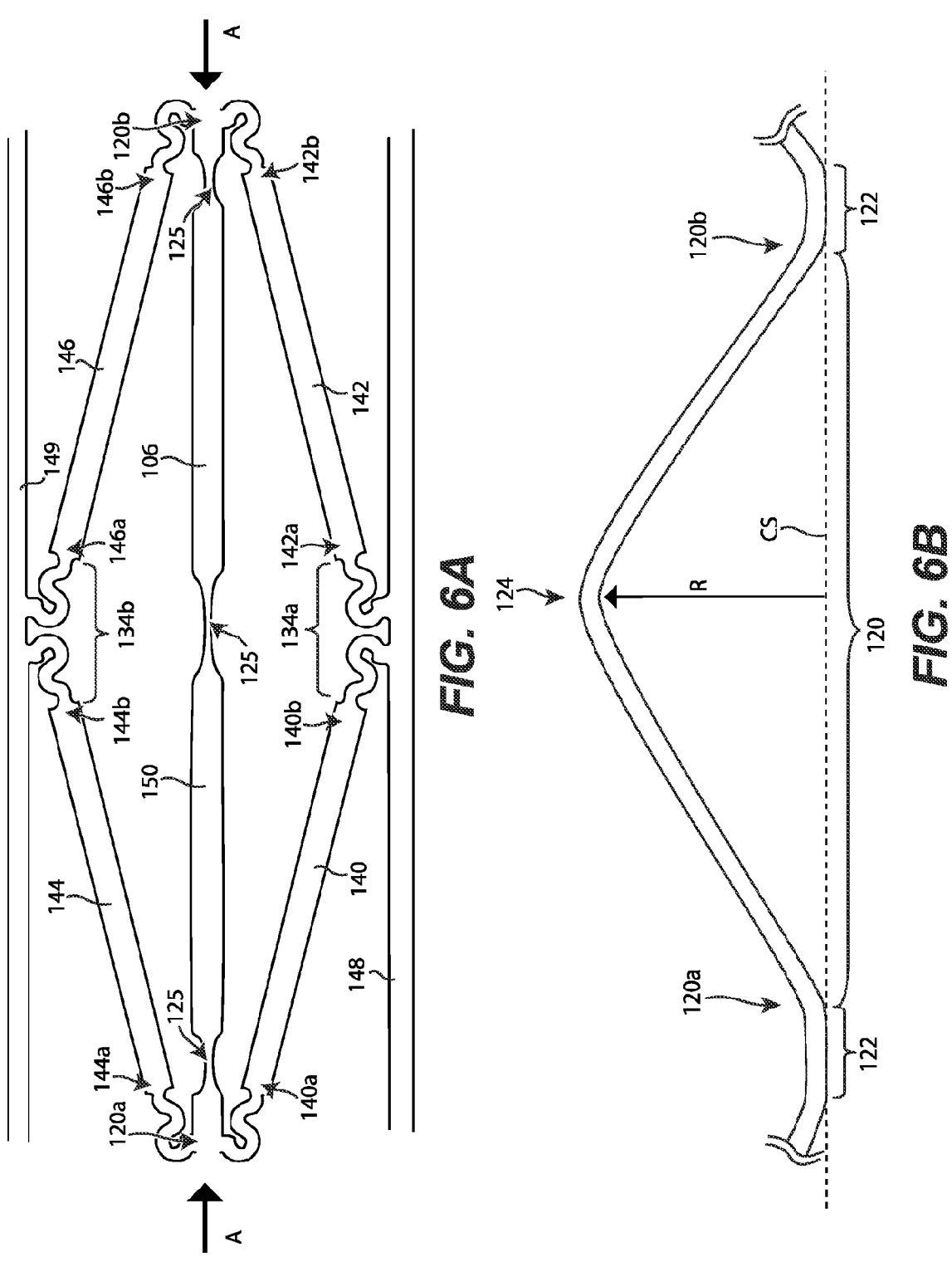
FIG. 6A is an enlarged portion of an expandable device configured in accordance with several embodiments of the present technology, shown in an expanded configuration.
FIG. 6B is a side view of a portion of a spine configured in accordance with the present technology, shown isolated from the portion of the expandable device in FIG. 6A.

In some embodiments, the thickness and/or width of the spines 106 (along the first portions 120 and/or second portions 122) may be varied to achieve a desired buckling profile, and/or all or portions of the spines 106 may be pre-formed with bends at particular locations and/or with particular shapes. One, some, or all of the first portions 120 may have a substantially constant thickness and/or width along their lengths (for example as shown in FIGS. 4A and 4B), which produces a single peak 124 and a more sinusoidal buckling profile. As shown in FIGS. 6A and 6B, in some embodiments one, some, or all of the first portions 120 may have a relief 125 at the desired peak location, and optionally near the first and second end portions 120a, 120b. The relief 125 may be formed by a length of the spine 106 having a reduced width (as shown), and/or may comprise a length of the spine 106 having a reduced thickness. Because of the reliefs 125, the resulting buckled portion 150 has tighter bends and takes on a more triangular shape, as shown in FIG. 6B. This peak may be relatively centered along the length of the spine, as shown in FIG. 6B, or it may be closer to one end of the spine, to give an asymmetric buckling profile. Additionally or alternatively, the reliefs 125 may be configured so that the buckled portions 150 have relatively flat peaks 124 (as compared to the "pointier" peaks 124 shown in FIG. 6B), thereby providing more surface area for engaging the apposing tissue, stent, balloon, or other device. The flatter peaks may also provide less traumatic surfaces for engaging different apposing materials.

Figures 7A, 7B:
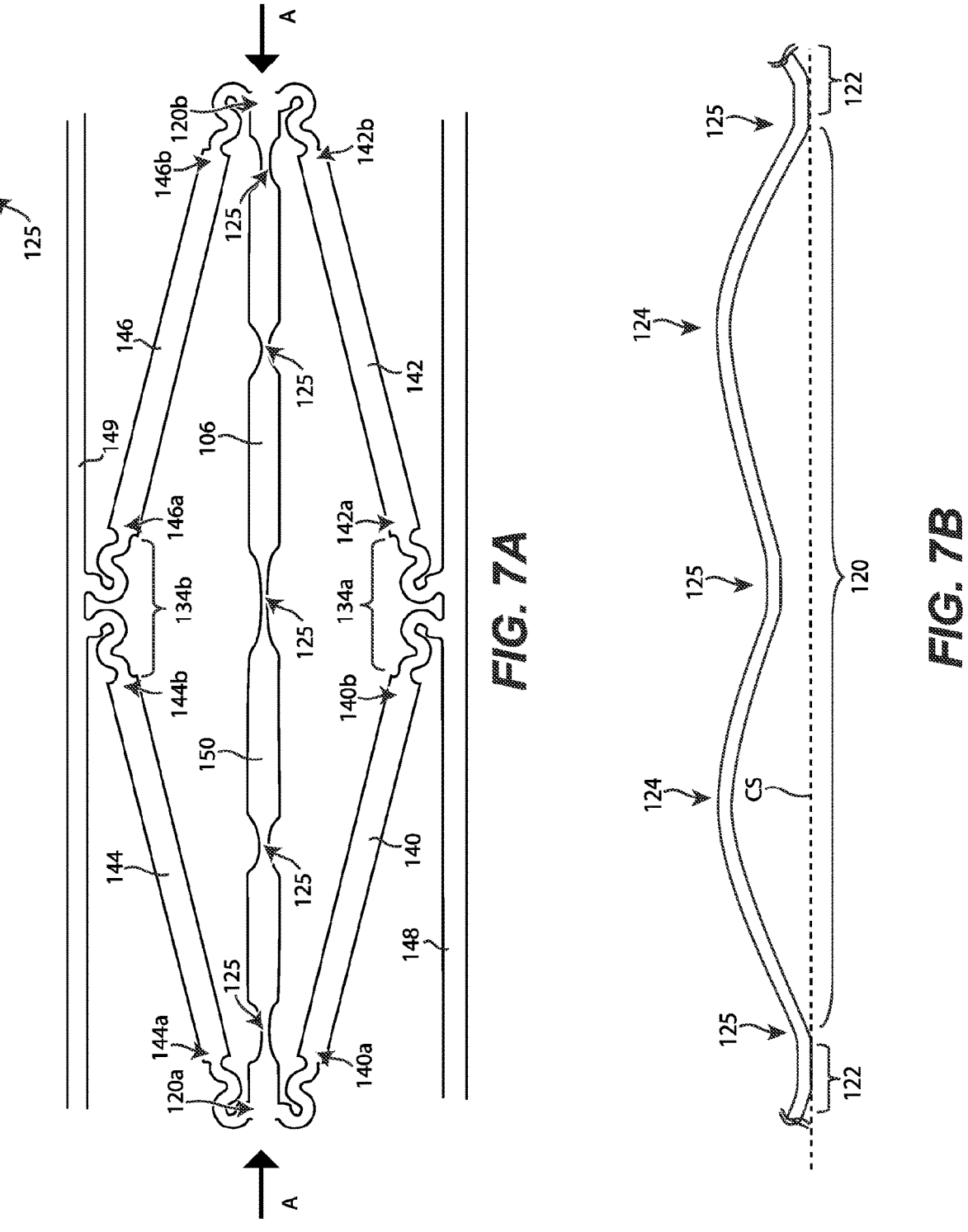
FIG. 7A is an enlarged portion of an expandable device configured in accordance with several embodiments of the present technology, shown in an expanded configuration.
FIG. 7B is a side view of a portion of a spine configured in accordance with the present technology, shown isolated from the portion of the expandable device in FIG. 7A.

In some embodiments, for example as shown in FIGS. 7A and 7B, one, some, or all of the first portions 120 may have multiple reliefs 125 such that the first portion 120 forms two or more buckled portions 150 (or two or more peaks 124) when the expandable device 100 and/or stent 101 is radially expanded. In such embodiments, the valley between the buckled portions 150 may be radially farther from the central longitudinal axis than the second portions 122 and/or struts 110. The first portions 120 along a particular spine 106: (a) may form the same or different numbers of buckled portions 150 per first portion 120, (b) may form buckled portions 150 having the same or different shapes or profiles, and/or (c) may be the same or different lengths. The first portions 120 within a particular spine region 121: (a) may form the same or different numbers of buckled portions 150 per first portion 120, (b) may form buckled portions 150 having the same or different shapes or profiles, and/or (c) may be the same or different lengths.

Figure 8:
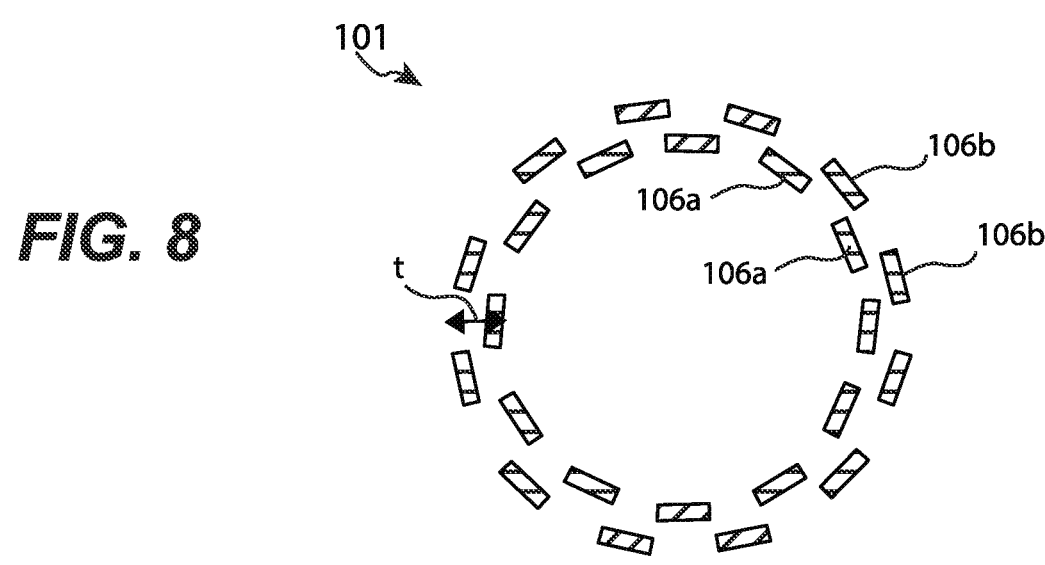
FIGS. 8 and 9 are axial cross-sectional views of expandable devices configured in accordance with embodiments of the present technology.
Figure 9:
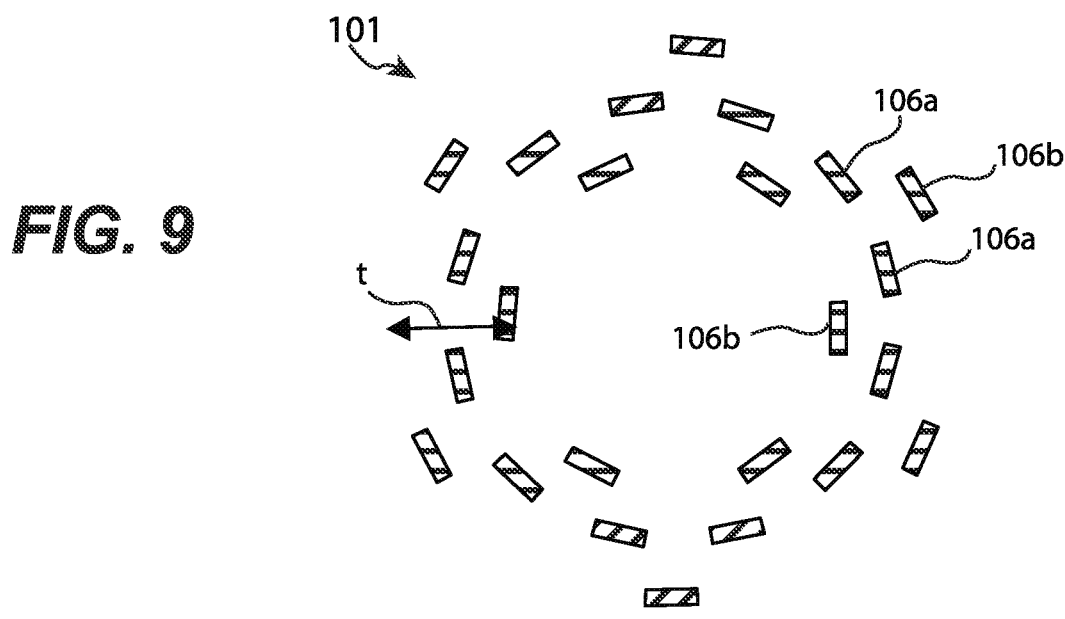

In some cases, as the stent 101 is expanded radially, the spines 106 might be inclined to buckle in different directions, with some buckling radially outward and some buckling radially inward. In some instances it may be preferable to encourage all of the buckled portions 150 to extend in the same direction. To encourage this, the stent 101 may be pre-formed (for example, via heat treatment) so that all of the first portions 120 of the spines 106 buckle in the same desired radial direction (i.e., radially inward or outward). For example, some or all of the stent 101 may be pre-formed to a relaxed, unconstrained diameter which is approximately the diameter of the overall delivery catheter, so that even after the expandable device has been delivered and the stent 101 is at its relaxed size, the relaxed device can be removed through the sheath or guiding catheter. In the case of a TAVR, that might be 14-21 Fr, or 4.7 mm-7 mm in diameter. Additionally or alternatively, as depicted in FIG. 8, in some applications it may be preferable to have all of the buckled portions 150 buckle radially inwardly. As shown in FIG. 9, in some embodiments the spines 106 may buckle radially inwardly and radially outwardly, thereby producing twice the thickness t as compared to a stent where all of the buckled portions 150 extend in the same radial direction.

Figure 10:
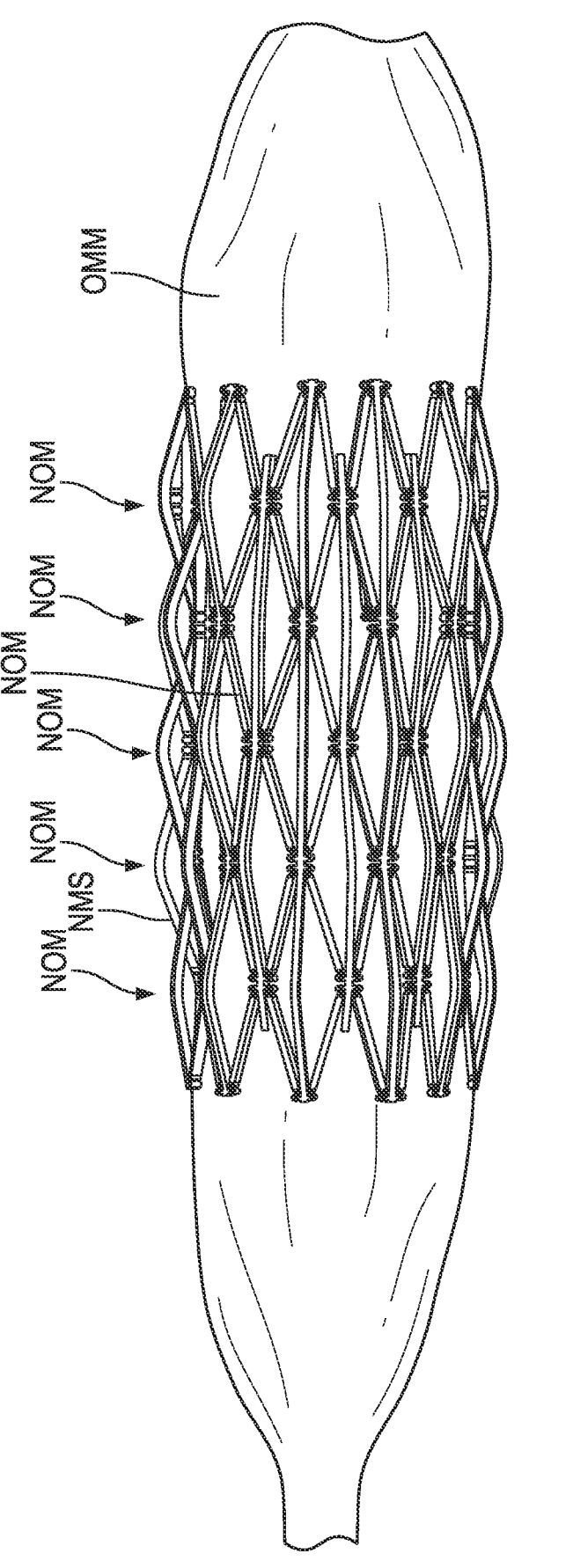
FIG. 10 is a side view of a treatment element configured in accordance with embodiments of the present technology.

As previously mentioned, the expandable device 100 and/or stent 101 may be expanded via expansion of a balloon placed in the main lumen 109 of the stent 101. An example of the expandable device 100 positioned over a balloon 200 is shown in FIG. 10.

According to some embodiments, the expandable device 100 and/or stent 101 of the present technology is self-expanding. For example, all or a portion of the stent 101 may comprise a material with superelastic properties, such as Nitinol. In some or all of such embodiments, the stent may form a small-diameter tube in its relaxed state. The expandable device 100 and/or stent 101 may also be heat treated and/or pre-shaped so that in its relaxed, unconstrained state it has a diameter that is less than the fully expanded diameter of the device. In such embodiments, the stent 101 may collapse down to its smaller relaxed diameter. Additionally or alternatively, the expandable devices 100 and/or stents 101 of the present technology may comprise a plastically deforming stent, such as a stent manufactured from a stainless steel or cobalt-chromium alloy.

In any of the embodiments disclosed herein, the buckled spines may be angled relative to the longitudinal axis of the stent.

III. Selected Embodiments of Expandable Devices for Endografting

The expandable devices 100 of the present technology provide distinct advantages when used for endografting. This may be particularly true in the case of aortic endografting. The buckled portions 150, for example, may form frictional elements which engage the native aortic wall to limit migration of the stent, at least in the short term.

In addition to the acute frictional engagement of the buckled portions with the aortic wall to limit migration in the short term, over the long term the buckled portions 150 might heal into the aorta wall, to make longer-term migration even more difficult. As vascular devices such as stents heal into a blood vessel, there is often a healing response which leads to the formation of smooth muscle cells around the foreign body. With the buckled portions 150, this healing response may lead to a stronger mechanical engagement with the aorta or vessel wall than would be the case with a stent of the prior art.

If the expandable devices 100 and/or stents 101 of the present technology are used as part of an aortic endograft and the buckled portions heal aggressively into the aorta wall, they might also prevent further dilation of the native aorta over the months and years following endograft placement. In many aortic endografting procedures, continued dilation of the aorta over time has been noted, leading to a separation of the aorta wall from the endograft, leading to leaks, renewed pressure on the native aneurysmal aorta wall, and potential rupture. The buckled portions 150 may heal permanently and aggressively to the aorta wall, thereby preventing long-term aortic wall dilation and separation from the endograft wall.

Figures 11, 12A, 12B:
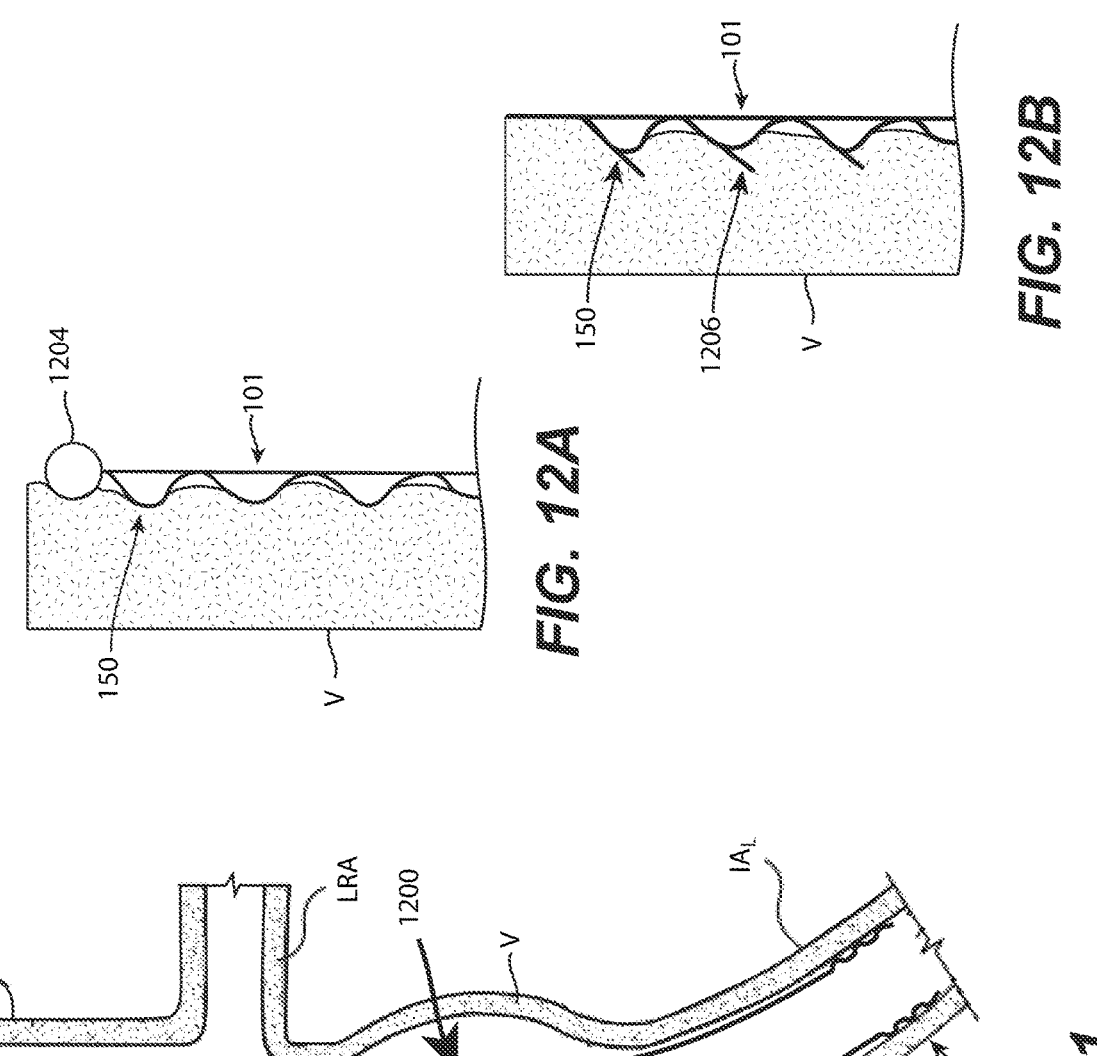
FIG. 11 shows an expandable device configured in accordance with embodiments of the present technology, shown positioned within an abdominal aortic aneurysm.
FIG. 12A is an enlarged view of a portion of an expandable device configured in accordance with embodiments the present technology, shown implanted at a treatment site within a body conduit.
FIG. 12B is an enlarged view of a portion of an expandable device configured in accordance with embodiments the present technology, shown implanted at a treatment site within a body conduit.

In some aortic endografting devices, it may be preferable to create buckled portions 150 at specific areas of the stent, such as at the ends of the stent where permanent ingrowth and healing into the vessel wall is desired. FIG. 11 shows an aortic endograft device configured in accordance with the present technology, shown positioned in the aorta across an abdominal aortic aneurysm ("AAA"). As shown, the device 1200 may comprise a stent with having end portions 1202 including buckled portions 150 to encourage ingrowth. In some embodiments, for example as shown in FIG. 12A, the stent may comprise a cuff 1204 (in addition to or instead of the buckled end portions 1202) of tubular graft material at the end portion of the expandable device 1200. The cuff 1204 may encourage an immediate seal between the endograft and the aortic wall (or wall of whatever body conduit in which the expandable device is placed) and limit any acute leaks into the annular space temporarily created by the buckled portions 150. In some embodiments, as shown in FIG. 12B, the stents of the present technology may include one or more securing members 1206. The securing members 1206, for example, may be positioned along one, some, or all of the first portions 120 such that radial expansion of the stent 101 and corresponding buckling of the first portions 120 actuates the securing members 1206 to project away from the buckled portions 150 and into the adjacent tissue. The securing members 1206 may be traumatic or atraumatic. The expandable devices and/or stents of the present technology may include securing members 1206 at other portions of the stent, instead of or in addition to the first portions 120. For example, the expandable devices and/or stents of the present technology may include securing members at one, some, or all of the second portions 122 of the spines 106 and/or at one, some, or all of the struts 110.

It will be appreciated that any of the foregoing concepts discussed with respect to endografting may also be applied to any of the embodiments discussed herein, regardless of the clinical application. For example, the end portions 1202, cuffs 1204, securing members 1206, etc. may be incorporated into any of expandable devices and/or stents discussed herein with reference to valvuloplasty, stent-valve delivery, and others.

In any of the embodiments detailed herein, including those for endografting, the stent may be self-expanding. A self-expanding form may be particularly beneficial as the seal between the device and the vessel wall may be less effective for balloon-expandable embodiments as an aneurysmal aorta degenerates. The row of endo-anchors disclosed herein may be configured to be repositioned, and thus may be repositioned in the short term allowing for more precise placement of the proximal neck and then more secure sealing with less migration as the buckled portions of the stent in-grow into the aortic wall in the long term.

IV. Selected Embodiments of Expandable Devices for Valvuloplasty

Figure 13:
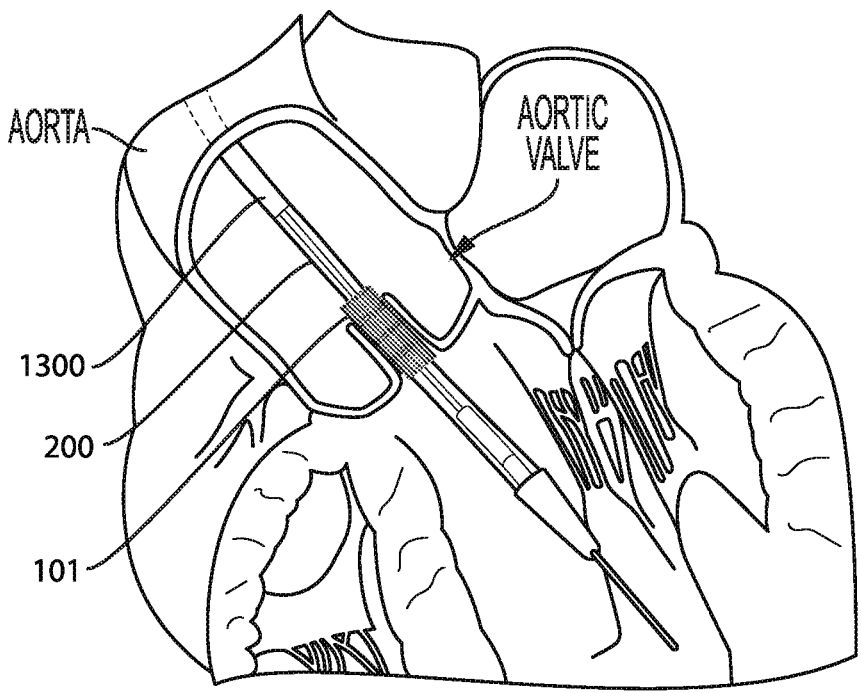
FIG. 13 illustrates an expandable device configured in accordance with embodiments of the present technology.

The expandable devices of the present technology may be configured for use in valvuloplasty procedures, and in particular those employing balloon-expandable stents. FIG. 13, for example, depicts an expandable device of the present technology, including stent 101, positioned in a collapsed configuration at a native valve annulus. FIG. 14A shows the stent 101 in an expanded configuration and positioned over an inflated balloon 200 at the native valve annulus. FIG. 14B is a cross-sectional view taken along line 14B-14B in FIG. 14A. In order to improve the effectiveness of valvuloplasty procedures, the stent 101 of the present technology can be placed over the outside of a tubular valvuloplasty balloon. At its compressed diameter (i.e., in the collapsed configuration), the wall thickness of the stent 101 may be as thin as the tubing from which it was cut. Therefore, the stent 101 would not add much to the compressed delivery profile of the overall device. As the balloon is expanded, the stent 101 may expand in diameter but the buckled portions 150 would create an additional thickness, so that it creates an open annular space 108 between its inner diameter and outer diameter through which blood can flow.

The expandable devices 100 and/or stents 101 of the present technology may have a number of positive effects on the valvuloplasty procedure. The perfusion capability enabled by the annular lumen of the stent 101 allows the valvuloplasty balloon 200 to remain inflated for a prolonged period of time, thereby enabling potentially better and more complete dilation of the stenosed valve. This might create a more complete and permanent valvuloplasty effect.

As the buckled portions 150 contact the native valve, they may apply a more concentrated force to a number of focal spots on the calcified valve and annulus. This higher localized force can render the valvuloplasty balloon more effective in breaking up calcifications and restoring more complete valve leaflet motion. The higher localized force may further increase the effective orifice area of the valve. In some cases it may be advantageous to do multiple inflations/deflations of the balloon 200. The expandable device 100 and/or stent 101 may be rotated or advanced or withdrawn between inflations so that the buckled struts 150 press against a number of different focal areas of the native valve and annulus, thereby achieving a more complete and effective valvuloplasty.

According to some embodiments, for example as shown in FIG. 15, the expandable device may comprise a stent (such as stent 101 described herein) and a sleeve of thin flexible material 1502 such as expanded polytetrafluoroethylene (EPTFE, or "Gore-Tex"), polyurethane, polyethylene, or other material positioned over the stent 101. The sleeve of material 1502 may be configured to act as a one-way valve to maintain aortic pressure and prevent regurgitation during the balloon inflation. The buckled portions 150 of the stent 101 may extend radially outwardly (as shown) and press against the native annulus and/or other adjacent tissue. In some embodiments, the buckling portions 150 extend radially inwardly. In some embodiments, some of the buckling portions 150 extend radially inwardly and some of the buckling portions extend radially outwardly. Additional details regarding one-way valves are provided elsewhere herein.

According to some embodiments, for example as shown in FIG. 16, the expandable device may be configured to filter or catch any embolic debris which is created during the valvuloplasty procedure. The expandable device may comprise, for example, a stent (such as stent 101 described herein) and a filter 1602 coupled to an end portion of the stent 101. The buckled portions 150 of the stent 101 may extend radially outwardly (as shown) and press against the native annulus and/or other adjacent tissue. In some embodiments, the buckling portions 150 extend radially inwardly. In some embodiments, some of the buckling portions 150 extend radially inwardly and some of the buckling portions extend radially outwardly.

It will be appreciated that any of the foregoing concepts discussed with respect to valvuloplasty may also be applied to any of the embodiments discussed herein, regardless of the clinical application. For example, the sleeve 1502, filter 1602, etc. can be incorporated into any of expandable devices and/or stents discussed herein with reference to endografting, stent-valve delivery, and others.

V. Selected Embodiments of Expandable Devices for Stent-Valve Delivery

Transcatheter aortic valve replacement (TAVR) is currently the most common approach for aortic valve replacement. It is more popular than surgical valve replacement, as it avoids the surgical trauma, recovery time, and other complications associated with surgery. The most popular type of TAVR system is a balloon-expandable TAVR device, such as the SAPIEN line of valves from Edwards Laboratories. (For ease of reference, the SAPIEN 1, 2, and 3 models are referred to herein generally as "SAPIEN".) The SAPIEN TAVR device is a valve made from bovine pericardial tissue mounted on a cobalt-chromium alloy stent. This SAPIEN stent-valve is compressed onto a deflated cylindrical balloon at the end of a delivery catheter. The stent-valve is then advanced into the patient's femoral artery and up the aorta to the aortic valve. The balloon is then inflated very quickly to expand the stent against the native aortic valve. After complete stent expansion is rapidly confirmed, the balloon is very quickly deflated.

Deflation of the balloon needs to happen very quickly, because while the balloon is inflated, the balloon occludes the aortic valve and there is no flow through the aortic valve. This causes a temporary decrease in systemic arterial pressure, which is not in itself a significant risk. But the fact that the left ventricle is unable to expel any blood means that with each heartbeat, more and more blood is pumped into the left ventricle and it expands more and more. This can cause dangerous and traumatic hyperexpansion or even rupture of the left ventricle. To prevent this from occurring, prior to the TAVR deployment a pacing catheter is introduced and screwed into the wall of the heart, and just prior to TAVR balloon inflation the heart is paced at a high rate of approximately 200 beats per minute. At 200 beats/minute, the ventricle has no time to dilate and fill between beats, so the dangerous overexpansion of the ventricle is prevented.

However, it is dangerous to pace the heart at this rapid pace for an extended period of time. Extended periods of rapid pacing during TAVR have been associated with atrial fibrillation, acute kidney injury, prolonged procedural hypotension, and higher overall mortality. Therefore, physicians strive to inflate and deflate the balloon quickly as possible, and the entire sequence of rapid pacing and stent-valve deployment is typically performed in less than half a minute. The addition of a pacing catheter also adds incrementally to the time, expense, and complexity of the overall TAVR implantation.

For the foregoing reasons, the TAVR deployment procedure is a relatively high-stress and high-risk procedure. The limited time available increases the risk of improper positioning of the valve, such as too low in the aortic root or too high above the annulus where a portion of the valve apparatus might block the coronary arteries. The rushed nature of balloon-expandable deployment procedures also increases the risk of incomplete deployment of the stent-valve. This can lead to either incomplete apposition of the stent against the aortic annulus, resulting in perivalvular leakage, or incomplete dilation of the annulus, leading to a non-circular final stent geometry. Incomplete dilation of the stent can significantly increase the incidence of increased valve leaflet wear and early valve failure.

For all of the foregoing reasons, it would be advantageous to have a balloon which allows flow through the aortic valve during the stent expansion process, to allow the physician to gradually and completely deploy the stent in exactly the right position, without any time pressure.

FIG. 17A shows the distal portion of a TAVR delivery assembly 1700 configured in accordance with several embodiments of the present technology. As shown in FIG. 17A, the delivery assembly may comprise a balloon 200 (shown in a deflated state in FIG. 17A) and shaped retaining elements under each end of the balloon 200 to hold the stent-valve (not shown) in place during delivery. FIG. 17B shows the same TAVR delivery assembly 1700 with a stent of the present technology (such as stent 101) superimposed over the portion of the balloon which holds the stent-valve. FIG. 17C shows the assembly 1700 with the balloon 200 inflated, expanding the stent 101 and a stent-valve 1702 (shown in cross-section), with blood flowing through the buckled stent 101.

FIG. 18A shows the same assembly shown in FIG. 17C, but with a tubular sleeve 1802 of thin flexible material such as EPTFE. The tubular sleeve 1802 may form a one-way valve to prevent regurgitation of blood backwards through the device during diastole. The tubular sleeve 1802 may be bonded to the most buckled portions 150 of the stent to hold it in place when it is inflated, while still allowing it to collapse and fold when the stent is collapsed. The proximal end of this sleeve 1802 might be crimped or sutured in a variety of ways to encourage the sleeve 1802 to close in diastole. One such way is shown in FIG. 18B. The sleeve

1802 might also be tethered to the shaft of the delivery catheter proximally, also as shown in FIG. 18B, to keep it in place and to prevent it from collapsing distally due to blood pressure.

In many cases, a relatively modest degree of buckling may be required to provide sufficient blood flow. To demonstrate, FIGS. 19A and 19B conceptually depict the cross-sectional area of an annular lumen 108 created by the expandable devices of the present technology (depicted in FIG. 19A), as compared to a circular lumen 111 (depicted in FIG. 19B). In this example, the outer diameter of the buckled spines 120 is 24 mm (or R=12 mm), and the diameter of the inner lumen 109 is 21 mm (or R=10.5 mm). In this case the thickness t of the annular lumen 108 is 1.5 mm, and the circumference of the annular lumen 108 is approximately 70 mm. Therefore, the cross-sectional area of the annular lumen 108 is approximately 105 square millimeters, which is approximately equivalent to the area of a cylindrical lumen 111 with a diameter of 11.6 mm (depicted in FIG. 19B). This provides more than enough cross-sectional area to allow the heart to pump blood into the aorta on a steady-state basis without an excessive pressure gradient. It will be appreciated that the foregoing dimensions are provided by way of explanation and do not limit the expandable devices and/or stents of the present technology as such.

According to some embodiments, the expandable device 100 and/or stent 101 may have a length of approximately 25 mm, designed to fit over the balloon where the valve is placed. Within a given spine region 121, the stent 101 may have a series of 12 first portions 120 and 24 pairs of struts 110 around its circumference, and may have 5 spine regions 121 over its length. Each of the spine regions 121 may comprise 12 first portions 120 that form 12 buckled portions 150 in the expanded configuration. In some embodiments, one, some, or all of the first portions 120 form more than one buckled portion 150 in the expanded configuration. At least for the purposes of this example, it is assumed that the buckled portions 150 are designed to buckle outwardly as the expandable device 100 and/or stent 101 is expanded. Thus, when the expandable device and/or stent is deployed, it may have 60 buckled portions 150 pressing the stent-valve outwardly. It will be appreciated that the foregoing details are provided by way of example only and that the expandable device 100 and/or stent may have more or fewer spine regions 121, first portions 120, buckled portions 150, struts 110, etc. (for example, as detailed in Section II). The buckled portions 150, in combination with the EPTFE sleeve, may spread the load very effectively over the area of the stent-valve and prevent any stress concentrations which might damage the stent-valve during deployment.

Figure 20:
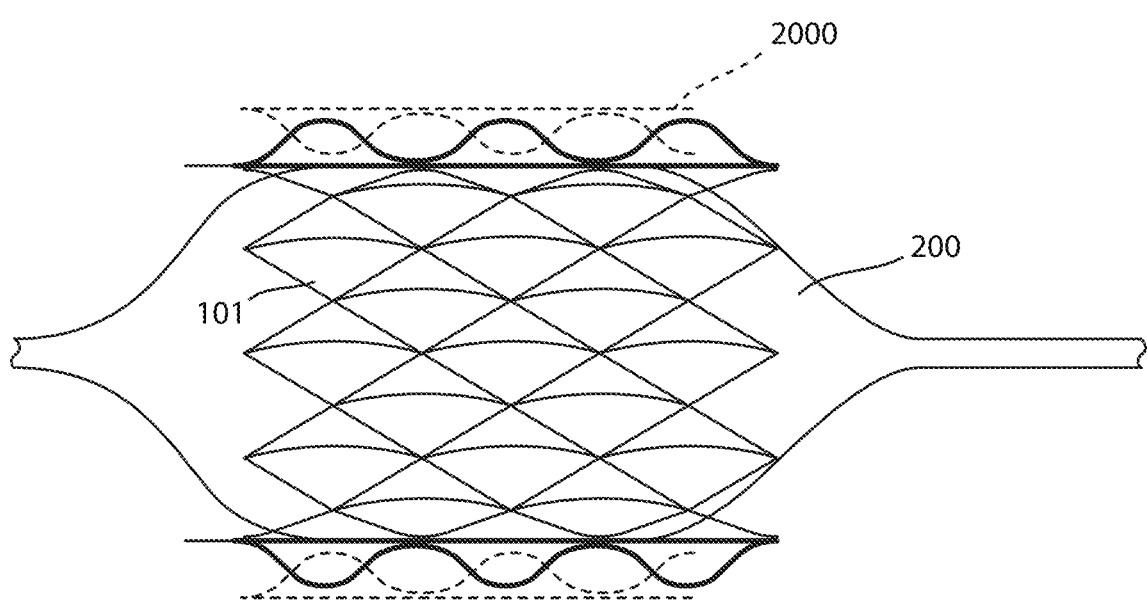

As described in the example above, the stent-valve might be supported in 60 places as it is deployed. In some embodiments, it might have the buckle portions 150 extending radially inward, and those 60 buckles pressing against the balloon. However, it might be advantageous to have both the balloon and the stent-valve be supported even more evenly during deployment, to limit any potential damage to the stent-valve. In addition, the expandable device may foreshorten somewhat as it expands. The TAVR stent-valve may also foreshorten somewhat, so the two stents may generally foreshorten together. In some cases it may be beneficial to have the surface of the expandable device not foreshorten as it expands. To accomplish this, for example as shown in FIG. 20, the expandable device may include a second stent 2000 outside of a first, buckling stent (such as stent 101) to provide additional support for the stent valve, with less foreshortening or no foreshortening at all. The first and second stents 101, 2000 may be connected at the ends so that the outer stent 2000 stays positioned on top of the buckled inner stent 101, effectively spreading its force over a broader area of the stent-valve.

It will be appreciated that any of the foregoing concepts discussed with respect to stent-valve delivery may also be applied to any of the embodiments discussed herein, regardless of the clinical application. For example, the sleeves, delivery devices, balloons, etc. can be incorporated into any of expandable devices and/or stents discussed herein with reference to endografting, valvuloplasty, and others.

VI. Selected Embodiments of Expandable Devices for Stenting

Expandable stents are widely used for expanding blood vessels and other body lumens, and for maintaining patency of blood vessels and other body lumens. These stents can be either balloon-expandable, typically made of cobalt-chromium or stainless steel alloys, or self-expanding, typically made of nickel-titanium (Nitinol) alloys. To expand a narrowed blood vessel or body lumen, the balloon pressure or expansive force of the Nitinol stent needs to overcome the resistance of the vessel to expansion. Often, the vessel is tightly stenosed and the vessel wall contains calcium deposits which render the vessel highly resistant to expansion. The calcium deposits may also lead to highly irregular expansion of the vessel. All of the stretching required to expand the vessel may occur on one side of the vessel rather than more equally around the circumference of the vessel.

In order to address these issues, angioplasty balloons have been developed with blades disposed about the circumference of the balloon, called "cutting balloons." These cutting balloons allow the vessel narrowing to be dilated more evenly, more completely, and with less balloon inflation pressure. Another approach is to use ultrasound energy to break up the calcium deposits during the dilation of the vessel. After the vessel is dilated with a cutting balloon or ultrasound-enhanced balloon, a stent is frequently placed to further open and maintain patency of the vessel lumen.

In some embodiments, the stents of the present technology can be configured as a cutting stent and/or used as a cutting stent. For example, as the stent expands, the spines could buckle radially outwards, forming pressure points which can crack the calcific lesions in the vessel more effectively and with less pressure. The spines may be shaped to enhance their ability to incise or crack the stenotic lesion in the vessel wall. This cutting stent might obviate the need for pre-dilation of the vessel with a cutting balloon. When the stent is fully expanded, the buckled spines can extend into the vessel wall so there is no reduction in final lumen diameter. As the vessel heals after the procedure, having the buckled spines healing into the vessel wall might help to stabilize the stent and the vessel, which might provide additional benefits. In some embodiments, the stent may include one or more blades, spikes, or cutting elements disposed on the spines. For example, the stent may include 3, 4 or 6 rows of spines around the circumference with cutting elements. In these and other embodiments, the edges of the struts and/or spines may be sharpened and/or otherwise configured to cut adjacent material or tissue.

VII. Other Design Details

Figure 21A:
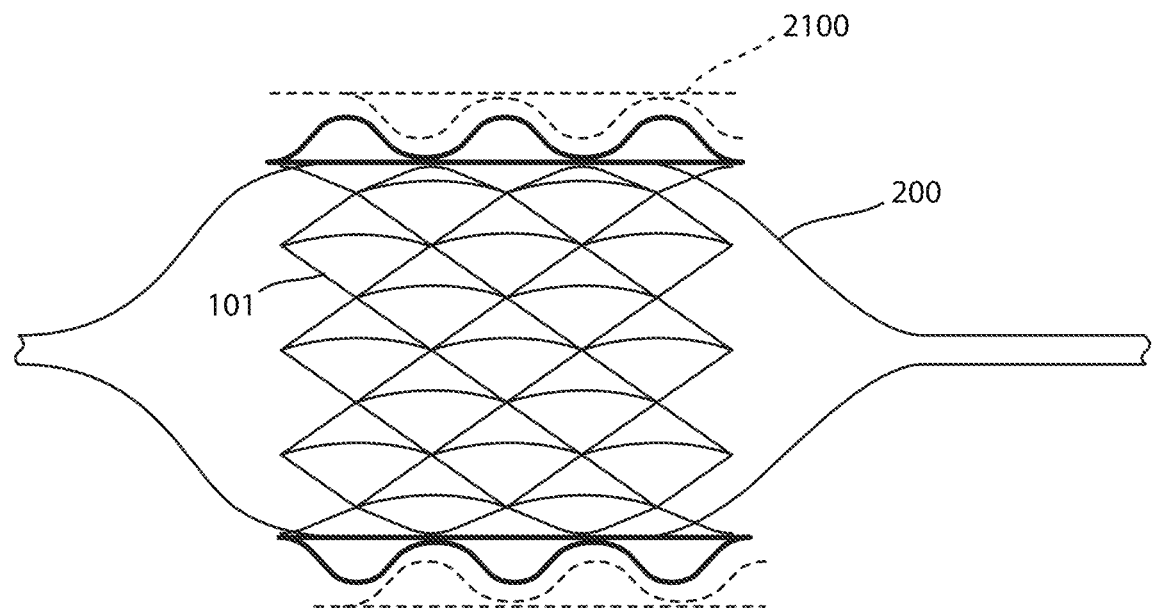
Figures 21B, 21C:
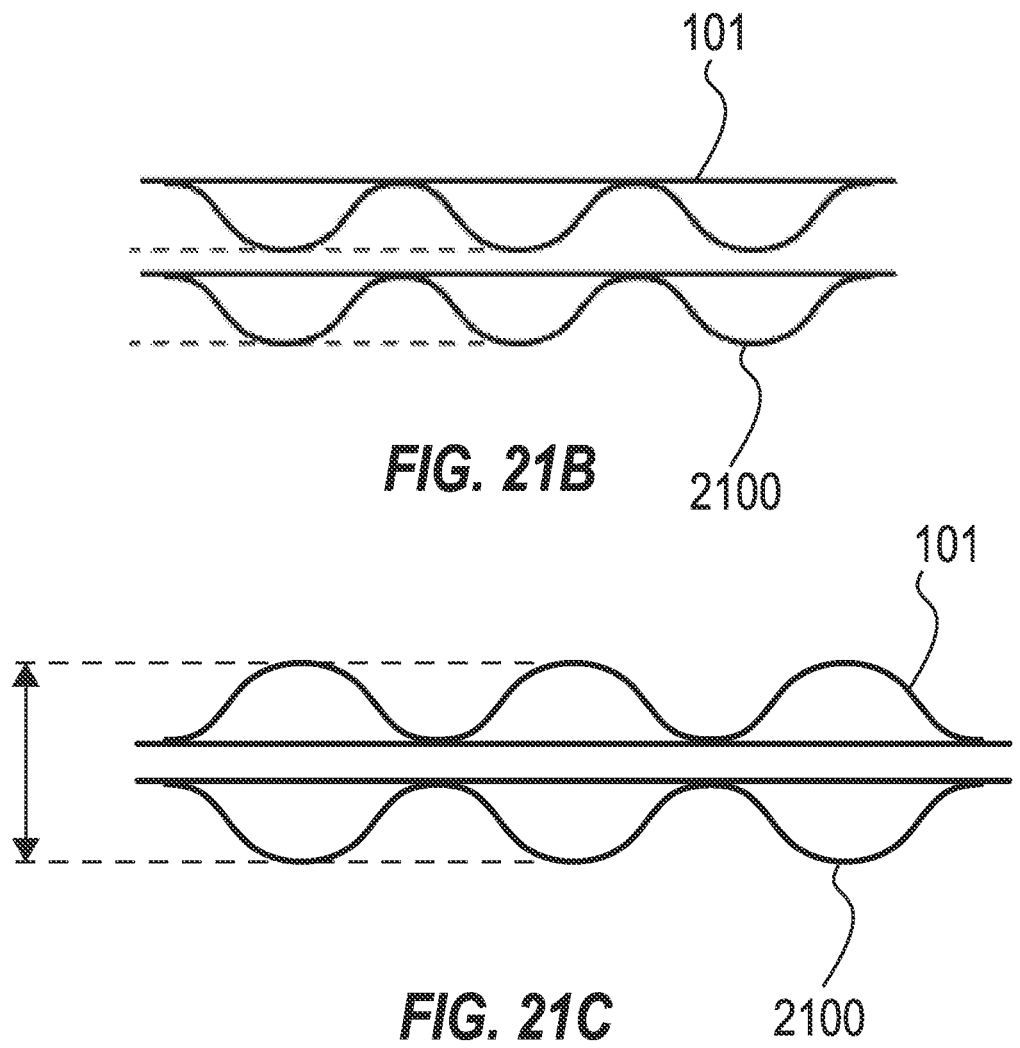

In some embodiments, the expandable device may comprise at least two nested stents, each having buckled portions. The stents may be arranged so that their buckled portions face towards and/or away from one another. Depending on how the outer buckling stent is positioned relative to the inner buckling stent, the outer stent may affect the annular thickness of the expandable device For example, as shown in FIG. 21A, it may be advantageous to configure the outer stent 2100 with the buckling elements predisposed to buckle radially inwards, and to position these buckles such that they follow the buckling elements of the inner stent 101. In this way, both the inner and outer surfaces will have flat diamond-shaped stent patterns, which will press against the balloon and the stent-valve, respectively. This will further minimize any trauma to the balloon or the stent-valve, and will make the overall composite buckled-stent even stronger with a minimal increase in wall thickness. In some embodiments, the outer stent may further increase the annular thickness of the expandable device, for example, as shown in FIG. 21B. As shown in FIG. 21C, in some embodiments the outer and inner stents may buckle in directions away from one another.

As the stent expands, there will be significant stresses within the stent. The swinging struts will be under tension as they expand and create the force which compresses and longitudinally foreshortens the buckling spines. The stent strut widths and hinge details are configured to accommodate these stresses.

Along an intermediate portion of the stent, since there are additional struts all around each cell of the stent, the stent should hold its cylindrical shape. However, at the ends of the stent, there may be nothing holding the free termini of the spines in the plane of the stent 101 when the stent is radially expanded. These free termini may be inclined to bend radially inwards or outwards. In some embodiments, these bending free termini can be employed as securing members (such as securing members 1206 described herein). However, in some embodiments such radial bending of the spines (or struts) at the end portions of the stent may not be preferable. To control these ends, any of the expandable devices and/or stents described herein, for example as shown in FIG. 22, may include one or more extension members 2202 extending beyond the end termini of one, some, or all of the spines 106 to help hold the spines 106 and other structural members of the stent 101 in the cylindrical surface of the non-buckled portions of the stent 101. The extension members 2202 might be connected at their other ends to solid rings which fit around the delivery catheter. These rings may slide longitudinally as the stent expands.

Additionally or alternatively, as shown in FIG. 23A, the expandable device may comprise a plurality of eyelets and/or loops 2302 at the ends of the spines 106 and a connector 2304 threaded through the eyelets 2302 to control the ends of the stent. In some embodiments, the eyelets or loops may additionally or alternatively be placed at other longitudinal locations along the stent. The connector 2304 may be, for example, a fiber or suture that is threaded in a zig-zag pattern through the eyelets 2302. As the stent expands, the spines will compress longitudinally and the zig-zag pattern will become circular, as shown in FIG. 23B. When the stent is fully expanded, the connector 2304 may be taut, limiting the expansion of the stent ends and keeping them from buckling outwards from the plane of the stent.

Figure 24:
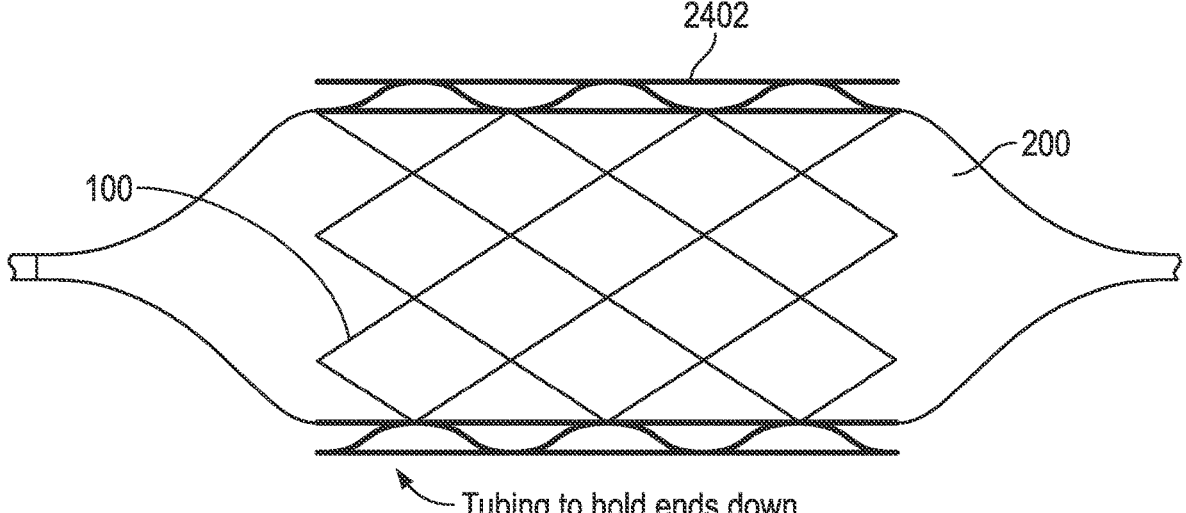

In some embodiments, for example as shown in FIG. 24, the expandable device may comprise a stent (such as stent 101) and a distensible tubing or fabric 2402, such as polyester, EPTFE, urethane, or thermoplastic elastomer on all or a portion of an inner surface of the stent. Should the expandable device be positioned around the outside of a cylindrical balloon 200, the tubing 2402 may prevent damage to the balloon 200 from any sharp stent edges or from the balloon 200 being pinched by the stent as it inflates or deflates. This tubing 2402 might also be wrapped over the ends of the stent and bonded to itself, as shown in FIG. 24, to help prevent the ends of the stent from bending outwards.

Figure 25:
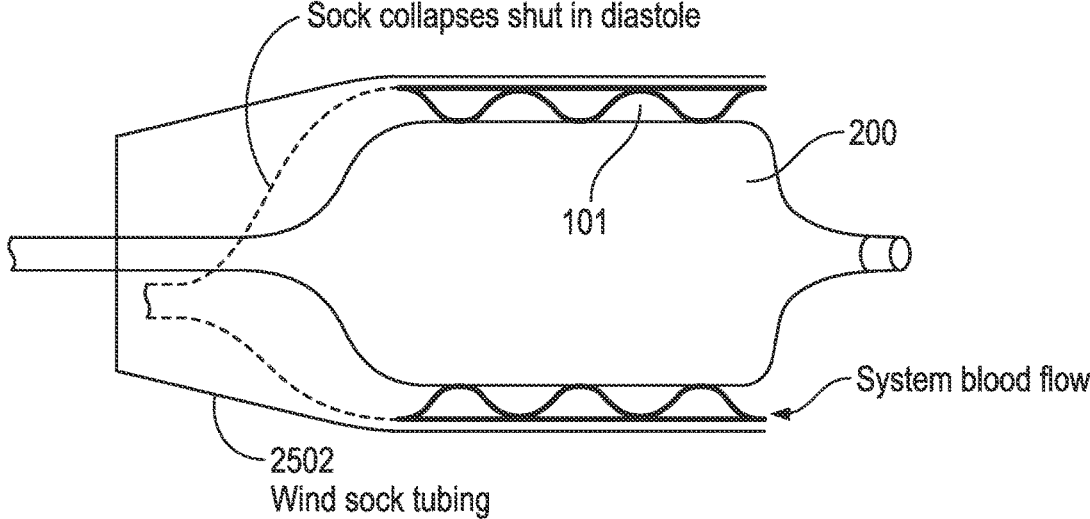

Additionally or alternatively, the expandable device may comprise a stent (such as stent 101) and a tubing or fabric, such as polyester, EPTFE, urethane, or thermoplastic elastomer extending proximally and/or distally from the stent to help hold the stent in place on the delivery catheter. An example of such an expandable device is shown in FIG. 25. The tubing or fabric 2502 may be configured to keep the stent from sliding proximally or distally as a stent-valve is delivered, and as the delivery catheter (not shown) is introduced and removed from the circulatory system. Instead of or in addition to a tubing, sutures, tethers, wires, or continuations of the stent itself might alternatively be used to prevent the stent from sliding proximally or distally.

Figure 26:
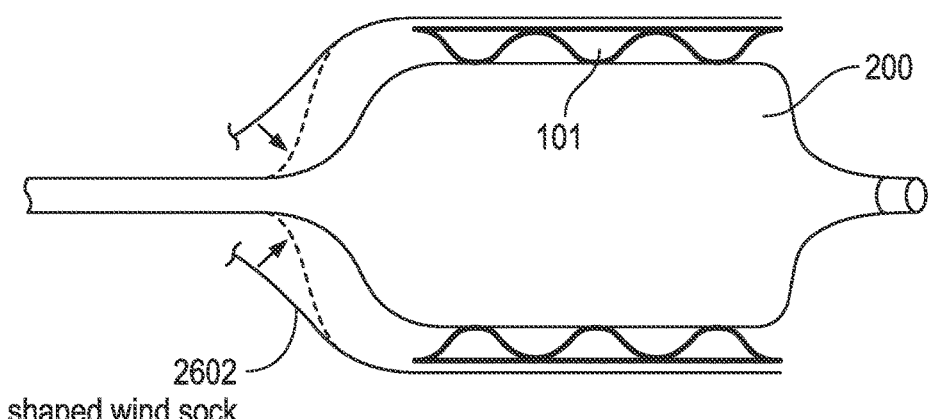
Figure 27:
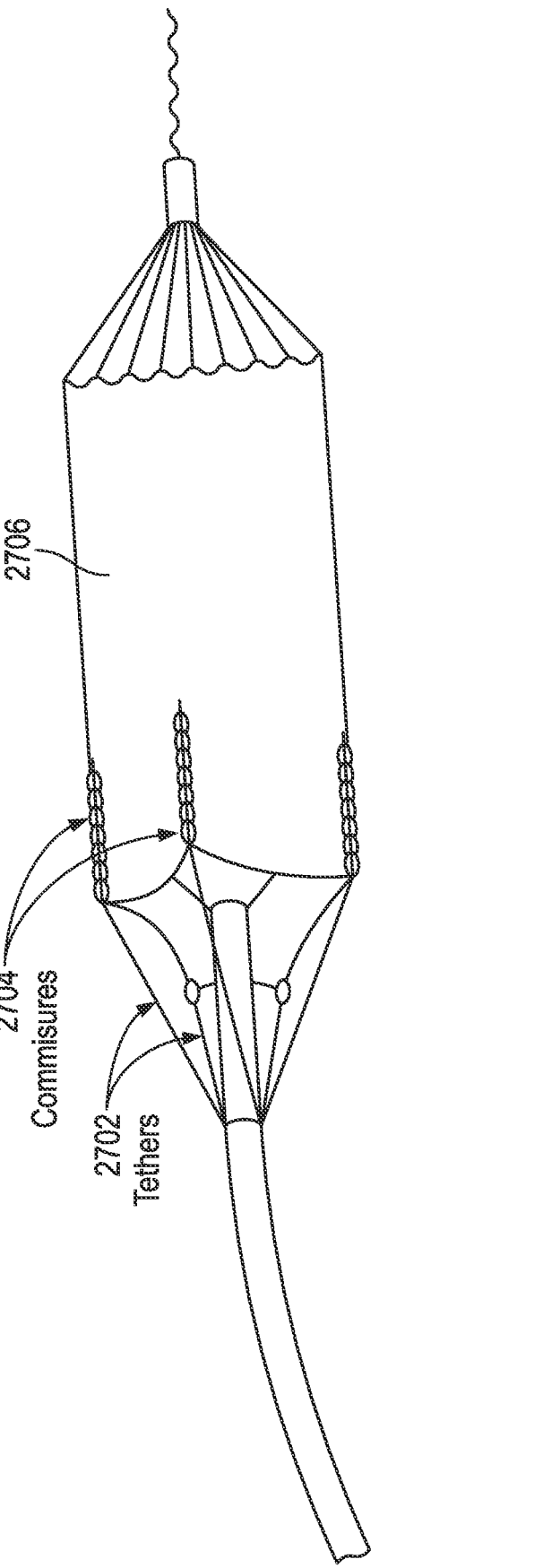

In some embodiments, for example as shown in FIGS. 25-27, the expandable device may comprise a stent (such as stent 101) and a cover (such as tubing or fabric) placed over all or a portion of an outer surface of the stent and/or all or a portion of an inner surface of the stent. The cover may perform several functions. For example, the cover may provide a protective barrier between the stent and the surrounding environment as the stent expands. The surrounding environment may be another device, such as a stent-valve or balloon, or both, and/or the surrounding environment may be native tissue, such as a native valve annulus or blood vessel wall. The cover can extend proximally or distally beyond the stent (depending upon the direction of blood flow) to form a valve which only allows one-way blood flow. This could be a tubular wind-sock valve 2502, which opens as blood flows through it in one direction, but collapses closed if the blood flows in the other direction, for example as shown in FIG. 25. The cover/valve material may be relatively cylindrical, or it may be tapered 2602 once it reaches the end of the balloon 200, for example as shown in FIG. 26. The wind-sock valve may close against the tapered end of the balloon 200. This might make the valve open and close very efficiently, with very little gradient but also little backflow of blood through the valve.

According to several embodiments, the tubular valve may be configured to preferentially close in discrete leaflets, such as two, three, four or five leaflets divided by commissures, as shown in FIG. 27. The commissures 2704 might be reinforced to create this shape, either by simply suturing some of the tubular fabric together to form stiffer commissures, or by sewing the commissures with some reinforcing element such as a metal wire or stiff polymer element. The tubular valve might also be reinforced with tethers, sutures, or wires between the end of the valve and the shaft of the delivery catheter, as shown in FIG. 27. In addition to improving the functionality of the valve, these tethers, sutures, or wires might also help to guide the stent and tubular valve into the sheath or guiding catheter during introduction or removal of the delivery catheter.

Figure 28:
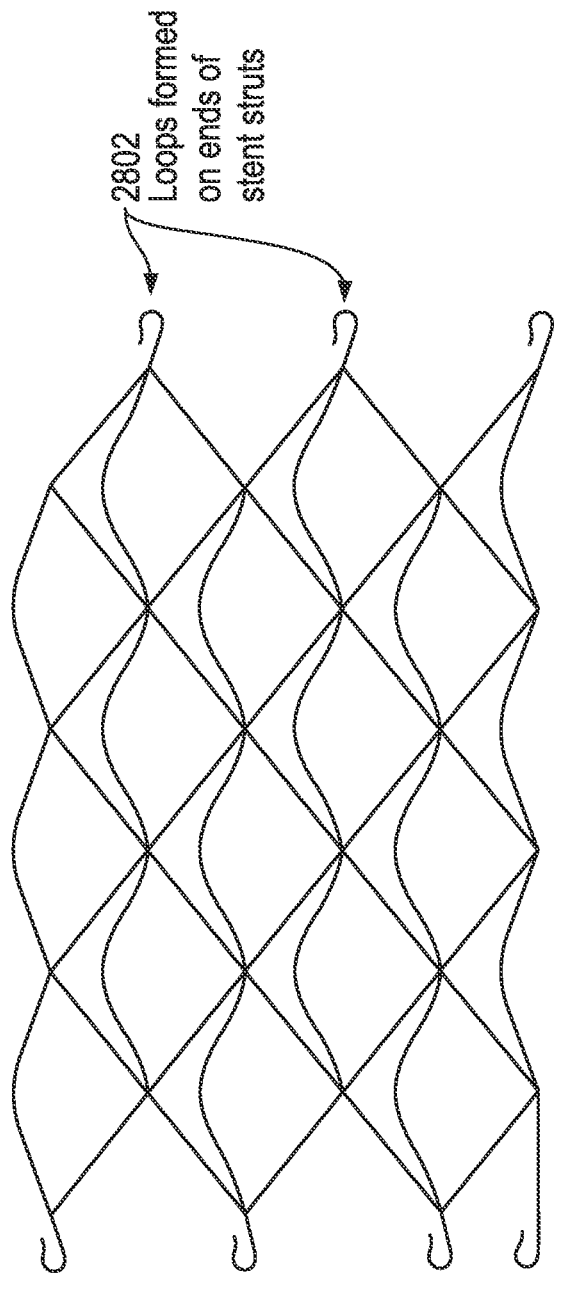

Even after rounding and electropolishing, the ends of the stent may have relatively sharp edges or points, which could damage the balloon, delivery catheter or stent-valve. It may be desirable to add loops 2802 or other protective features at ends of stent struts to prevent damage to the balloon, stent-valve, or delivery catheter, as shown in FIG. 28.

VIII. Balloon Strength

The force required to expand the expandable devices and/or stents of the present technology may apply incremental pressure on the underlying balloon (or other expandable element). Therefore, to apply the same radial expansion force to a stent-valve or native valve, it may be beneficial to inflate the balloon to a higher pressure as compared to the pressure required for a balloon when expanding a conventional stent. In order for a balloon to tolerate inflation to higher pressures, the balloon typically needs a stronger, thicker wall. However, this need for additional balloon inflation pressure is ameliorated by the fact that the stent will also support the balloon in any localized area where it might be inclined to plastically deform and burst, thereby effectively reinforcing the balloon via its encirclement of the balloon. If the balloon 200 deforms slightly into the spaces between the structural members of the stent (such as the spines and/or struts), that would also reduce the localized radius of curvature, as shown in FIG. 29. According to Laplace's insights on the relationship between radius of curvature and pressure, this would also reduce the wall stress on the balloon. Finally, the balloon diameter with the stent of the present technology might be 2-4 mm smaller than it would be without the stent. Smaller-diameter balloons require less wall strength than larger-diameter balloons, so for this reason the balloon may not need to be as strong and/or may not need as thick a wall. Additionally or alternatively, extendable elements (such as those described with reference to FIG. 22) can reinforce the tapered regions of balloons as another way to reduce required balloon wall strength. Reducing required balloon wall strength facilitates a reduction in balloon wall thickness or alternative balloon materials, both of which can be advantageous for reasons such as reducing packing density or required cross sectional area.

IX. Selected Examples of Manufacturing

In some embodiments, the expandable device may be formed by laser-cutting the desired pattern into a tubular sheet of material. In certain embodiments, the expandable device may be initially formed as a flat sheet of material having a pattern of struts and spines. The struts and spines may be formed by depositing a thin film on a flat surface in the desired pattern, or by laser-cutting a desired pattern into the flat sheet of material. The flat pattern may then be curled up into a generally tube-like shape such that the longitudinal edges of the flat pattern are positioned adjacent to or in contact with one another. The longitudinal edges can be joined (e.g., via laser welding) along all or a portion of their respective lengths. In some embodiments, the struts and spines may be formed by depositing a thin film on the surface of a tubular frame in a desired pattern (e.g., via thin film deposition, vapor deposition, or combinations thereof).

According to several embodiments, all or a portion of the stent may be heat treated in its desired fully expanded configuration, or in a configuration having a diameter smaller than is intended when the stent is implanted. Heat treating the stent may be beneficial for preferential bending at certain locations and may reduce or substantially remove any stresses that accompany forcing the stent from its collapsed or unexpanded configuration into the expanded configuration. To help achieve a desired shape in the expanded configuration, one or more portions of the stent may be thinned to form a preferential bending location.

In some embodiments, the stent 101 could be formed at an intermediate diameter between its constrained state and fully expanded state as a way to reduce the amount of strain that hinge connectors are exposed to in a given direction (if the hinge connector opens by 60 degrees from tubular to expanded state, then heat shaping at 30 degrees open allows the hinge connector to only experience 30 degrees of deflection from its heat-shaped state; this could potentially reduce the likelihood of fracture at hinges). In some embodiments, the self-expanding stent 101 could be heat treated and/or pre-shaped so that in its relaxed, unconstrained state it is fully expanded.

As described herein, in some cases it may be beneficial to pre-expand the stent just enough to ensure that the struts buckle in the desired direction. This pre-expansion processing could be as simple as expanding the stent on a very gently tapered mandrel, making sure that all of the struts are buckled in the right direction (radially inward or outward), and then annealing the stent in this shape. If it is desired to have the struts buckle radially inward, the tapered forming mandrel might have longitudinal slots into which the struts can buckle. The ends of the stent also could be folded over longitudinally to form softer rounded ends if desired. In these and other embodiments, a more detailed forming tool or tools can be used which conform to every detail of the desired stent shape. These forming tools can include holders configured to hold the stent from the outside as well as inside.

After any pre-forming and annealing, the stent may optionally be electropolished to minimize any sharp edges which might create foci for cracks, or damage the balloon, the stent-valve, or any adjacent tissue. Additionally or alternatively, the stent can be coated with a polymeric material or other material to improve compatibility with other elements of the system.

Conclusion

Although many of the embodiments are described above with respect to systems, devices, and methods for treating cardiac disease, the technology is applicable to other applications and/or other approaches, such as pulmonary or cerebral applications. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 2A-29.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Where a range of values is provided, it is understood that each intervening value, to the tenth of the unit of the lower limit unless the context clearly dictates otherwise, to between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

We claim:

1. An expandable device comprising:
a stent comprising a tubular sidewall, the sidewall of the stent having first portions and second portions, wherein the stent has a collapsed configuration and an expanded configuration in which the device is configured to be positioned within a body conduit of a human patient at a treatment site, and wherein each of the second portions has a first end and a second end, each of the first and second ends connected to an adjacent first portion via a joint having a sinusoidal shape, and
wherein transformation of the stent from the collapsed configuration to the expanded configuration causes the first portions of the sidewall to bow out of a cylindrical surface defined by the second portions of the sidewall such that, at least in the expanded configuration, the first portions form a plurality of buckled regions extending radially away from the second portions of the sidewall.

2. The expandable device of claim 1, wherein the buckled regions are spaced apart about a circumference of the stent.

3. The expandable device of claim 1, wherein the buckled regions are spaced apart along a length of the stent.

4. The expandable device of claim 1, wherein the buckled regions are disposed only at one or both of the first and second portions of the stent.

5. The expandable device of claim 1, wherein the buckled regions are disposed only along an intermediate portion of the stent.

6. The expandable device of claim 1, wherein, when the stent is in the collapsed configuration, the first and second portions are generally radially aligned such that the sidewall has a substantially cylindrical shape.

7. The expandable device of claim 1, wherein, when the stent is in the expanded configuration, the second portions are generally radially aligned along a length of the stent and the first portions are radially offset from the second portions.

8. The expandable device of claim 1, wherein, when the stent is in an expanded configuration, at least some of the buckled regions extend radially outwardly from the second portions.

9. The expandable device of claim 1, wherein, when the stent is in an expanded configuration, at least some of the buckled regions extend radially inwardly from the second portions.

10. The expandable device of claim 1, wherein, when the stent is in an expanded configuration, the buckled regions comprise arched protrusions, and wherein each of the arched protrusions have (a) first and second end portions coupled to one of the second portions and (b) a peak region between the first and second end portions, the peak region comprising a portion of the buckled region that is radially farthest from the first and second end portions.

11. An expandable device comprising:
a stent having a collapsed configuration and an expanded configuration in which the stent is configured to be positioned in a body conduit of a patient, the stent comprising a plurality of spines and a plurality of struts, the spines extending along a longitudinal axis of the stent and the struts extending between circumferentially adjacent spines, each of the spines having first portions and second portions along a respective length of the spine, wherein:
in the collapsed configuration, the struts and the spines are the same radial distance from a central longitudinal axis of the stent and together define a cylindrical surface surrounding a lumen, and
in the expanded configuration, (a) the struts and the first portions of the spines are a first radial distance from the central longitudinal axis, and (b) the second portions of the spines are a second radial distance from the central longitudinal axis, the second radial distance different than the first radial distance.

12. The expandable device of claim 11, wherein, when in the expanded configuration, the stent includes an annular lumen between (a) the second portions of the spines and (b) the struts and the first portions of the spines.

13. The expandable device of claim 12, wherein, when the stent is in the expanded configuration, the struts and the first portions of the spines together define an expanded lumen through the stent, and wherein the annular lumen surrounds the expanded lumen.

14. The expandable device of claim 12, wherein, when the stent is in the expanded configuration, the second portions of the stent together define an expanded lumen through the stent, and wherein the annular lumen surrounds the expanded lumen.

15. The expandable device of claim 11, wherein the second radial distance is greater than the first radial distance.

16. The expandable device of claim 11, wherein the second radial distance is less than the first radial distance.

17. The expandable device claim 11, wherein the second radial distance for some of the second portions is less than the first radial distance, and the second radial distance for others of the second portions is greater than the first radial distance.

18. The expandable device of claim 11, wherein the spines are substantially linear in the collapsed configuration and have an undulating shape in the expanded configuration.

* * * * *